US012687439B2

(12) United States Patent
Arias et al.

(10) Patent No.: US 12,687,439 B2
(45) Date of Patent: Jul. 21, 2026

(54) SCALABLE AND HIGH-PERFORMANCE PRESSURE SENSORS FOR WEARABLE ELECTRONICS

(71) Applicant: The Regents of the University of California, Oakland, CA (US)

(72) Inventors: Ana Claudia Arias, Lafayette, CA (US); Xiaodong Wu, Berkeley, CA (US); Yasser T. Khan, Albany, CA (US); Jonathan KangYu Ting, Berkeley, CA (US); Natasha Ariane Diniz Yamamoto, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 899 days.

(21) Appl. No.: 17/503,999

(22) Filed: Oct. 18, 2021

(65) Prior Publication Data

US 2022/0146340 A1 May 12, 2022

Related U.S. Application Data

(63) Continuation of application No. PCT/US2020/028503, filed on Apr. 16, 2020.

(Continued)

(51) Int. Cl.
*G01L 1/20* (2006.01)
*A43B 3/44* (2022.01)
(Continued)

(52) U.S. Cl.
CPC ................ *G01L 1/205* (2013.01); *A43B 3/44* (2022.01); *A43B 17/00* (2013.01); *A61B 5/6807* (2013.01);
(Continued)

(58) Field of Classification Search
CPC ....... G01L 1/205; G01L 19/0092; A43B 3/44; A43B 17/00; A61B 5/6807;
(Continued)

(56) References Cited

U.S. PATENT DOCUMENTS

| | | | | |
|---|---|---|---|---|
| 6,155,120 A | * | 12/2000 | Taylor .................. | A61B 5/1036 73/862.046 |
| 2015/0059486 A1 | * | 3/2015 | Choong ................ | G01L 9/0052 73/727 |

(Continued)

FOREIGN PATENT DOCUMENTS

| | | |
|---|---|---|
| KR | 1020150028125 B1 | 3/2015 |
| WO | WO 2018213937 A1 | 11/2018 |

OTHER PUBLICATIONS

Written Opinion of the International Searching Authority for PCT/US2020/028503 from the International Searching Authority, dated Jul. 29, 2020.

*Primary Examiner* — Tse W Chen
*Assistant Examiner* — Joseph A Tombers
(74) *Attorney, Agent, or Firm* — Leydig, Voit & Mayer, Ltd.

(57) ABSTRACT

Flexible pressure sensors and wearable devices incorporating one or more flexible pressure sensors, and methods of making the same. A flexible pressure sensor includes a first layer including a plurality of pressure-sensitive microstructures, and a second layer including one or more electrode pairs, each of the one or more electrode pairs including a first electrode positioned adjacent a second electrode on the second layer. The first and second electrodes may be positioned on the second layer in a side-by-side configuration.

8 Claims, 21 Drawing Sheets

Screen mesh mold — Hot press mesh mold into PS template — Peel off mesh mold — PS template with inverse mesh structure Spray-coat CNT on PS template — Cast PDMS precursor — Cure and peel off PDMS layer — Microstructured PDMS/CNT film

Related U.S. Application Data

(60) Provisional application No. 62/835,129, filed on Apr. 17, 2019.

(51) Int. Cl.

| | | |
|---|---|---|
| *A43B 17/00* | (2006.01) | |
| *A61B 5/00* | (2006.01) | |
| *G01L 19/00* | (2006.01) | |

(52) U.S. Cl.
CPC .. G01L 19/0092 (2013.01); *A61B 2562/0247* (2013.01)

(58) Field of Classification Search
CPC .......... A61B 2562/0247; A61B 5/4205; A61B 5/021; A61B 5/1038
See application file for complete search history.

(56) References Cited

U.S. PATENT DOCUMENTS

| | | | |
|---|---|---|---|
| 2019/0246734 A1* | 8/2019 | Nurse .................... | A61B 5/742 |
| 2020/0008299 A1* | 1/2020 | Tran ..................... | H05K 1/0386 |
| 2022/0128420 A1* | 4/2022 | Tee ......................... | G01L 1/205 |

* cited by examiner

Wearable pulse sensor     Pressure sensitive e-skin     Multifunctional smart insole Screen mesh mold     Hot press mesh mold into PS template     Peel off mesh mold     PS template with inverse mesh structure Spray-coat CNT on PS template     Cast PDMS precursor     Cure and peel off PDMS layer     Microstructured PDMS/CNT film Px6 pressed with 1.2 g object Px6 pressed with 2.4 g object Px6 pressed with 3.6 g object

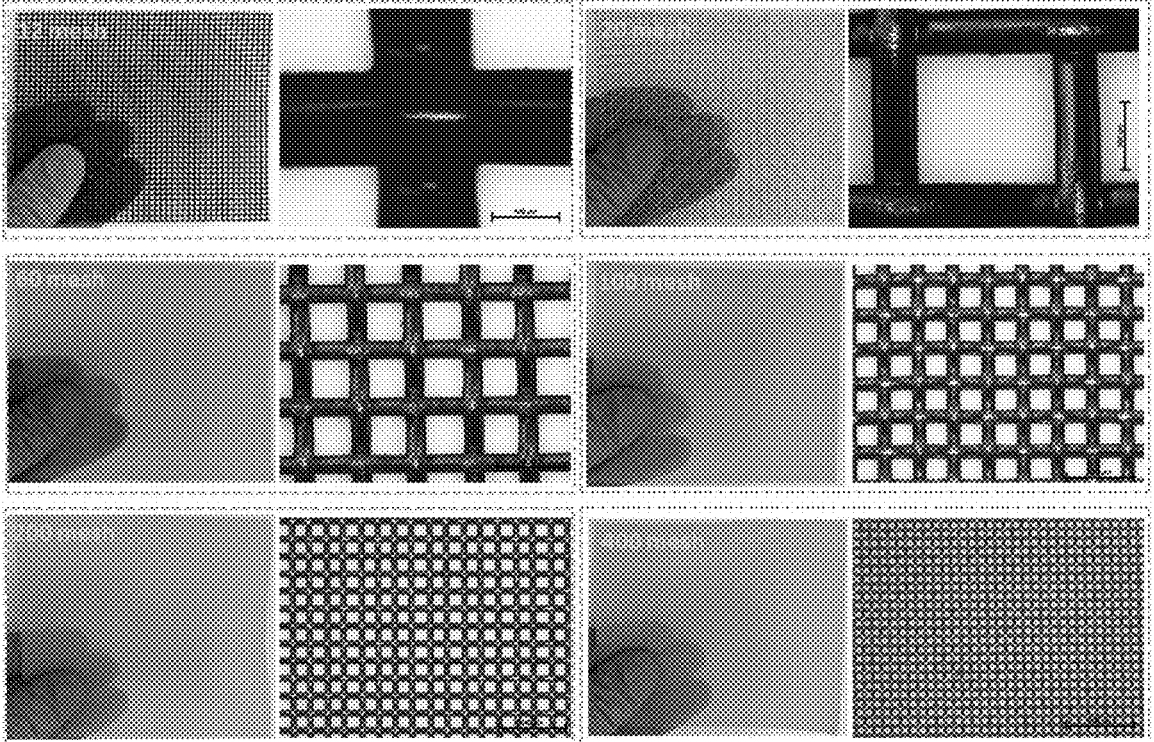
Fig. 7. Photographs and optical images of screen meshes with different microstructure sizes.

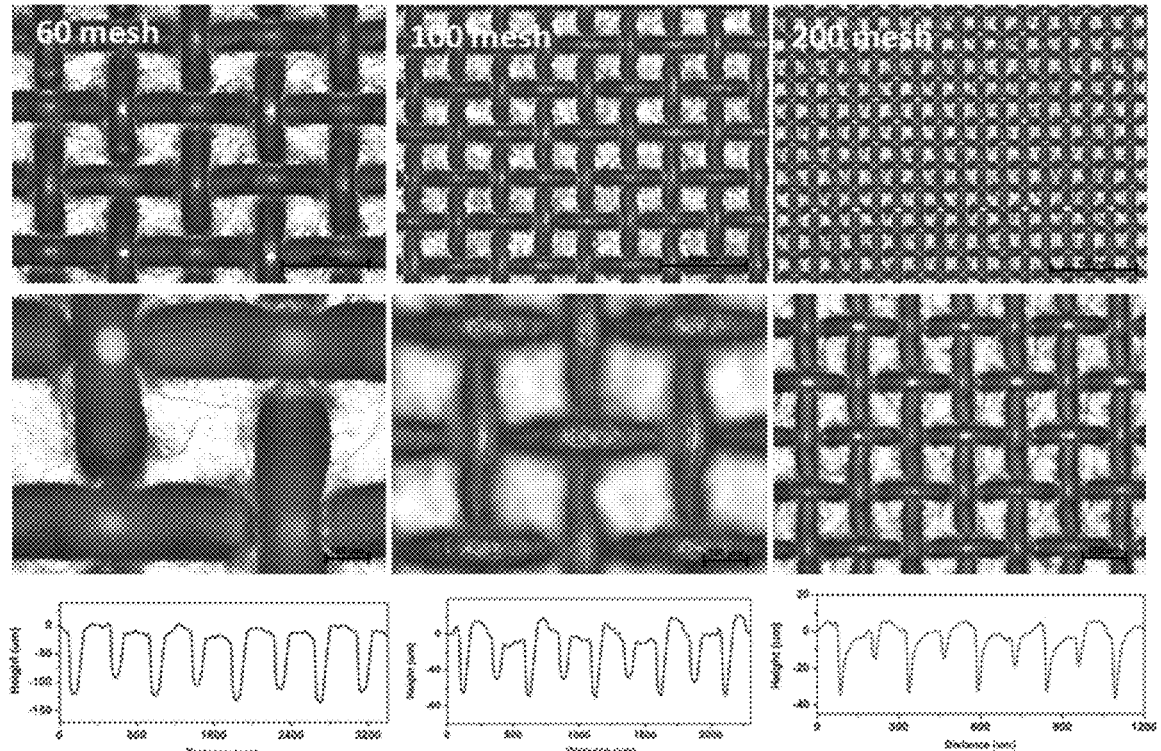
Fig. 8. Optical images and surface profiles of the reversed microstructures created on PS templates

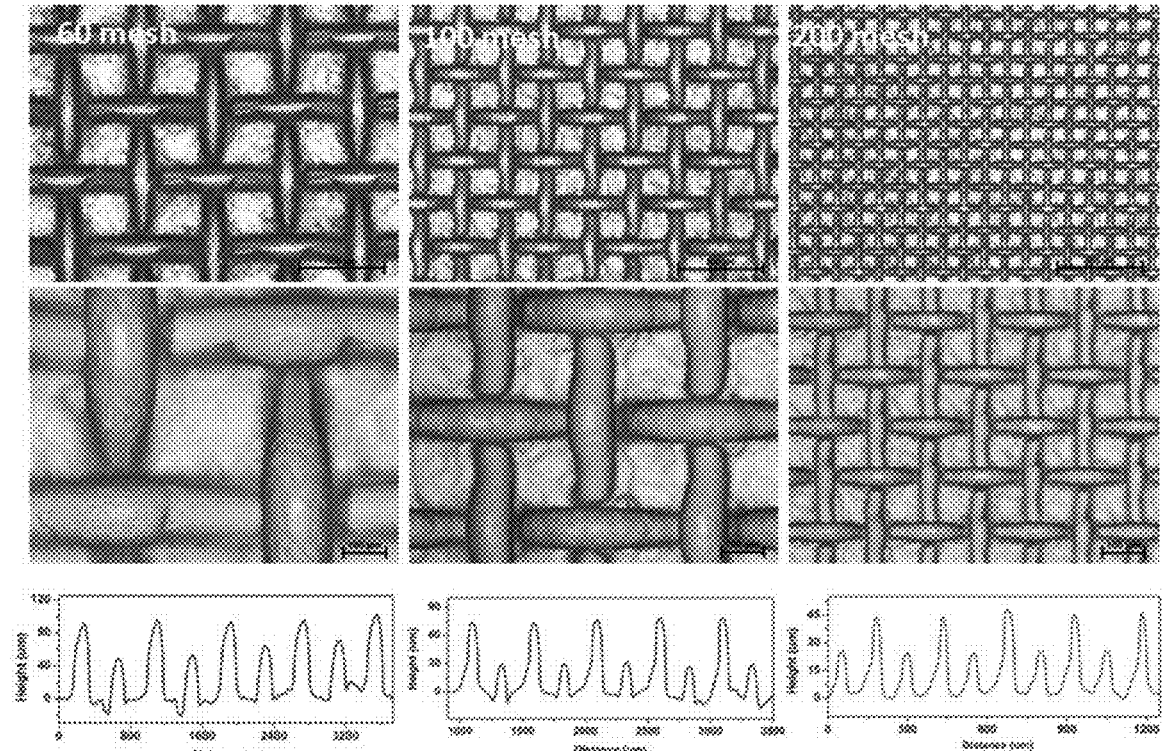
Fig. 9. Optical images and surface profiles of PDMS microstructures molded from different screen meshes (60, 100 and 200 mesh count, respectively).

FIG. 10A                                    FIG. 10B

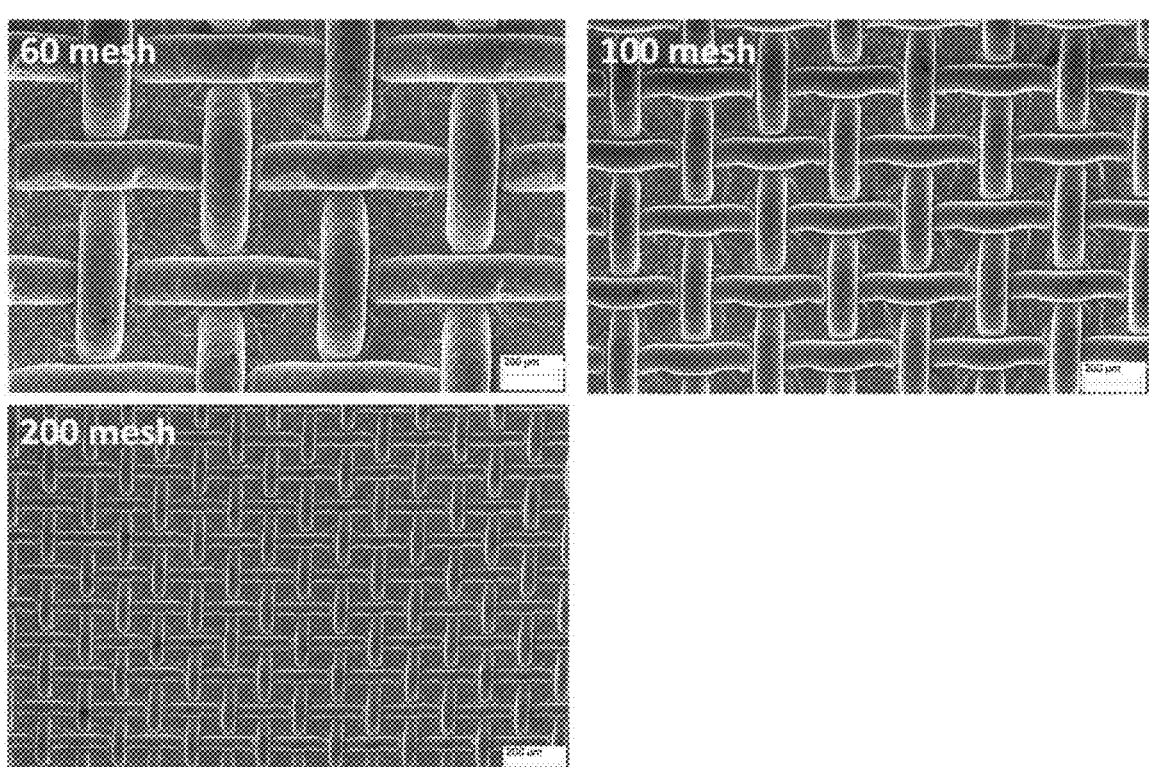
Fig. 11. SEM images of conductive PDMS/CNT microstructures molded from different screen meshes (60, 100 and 200 mesh count, respectively).

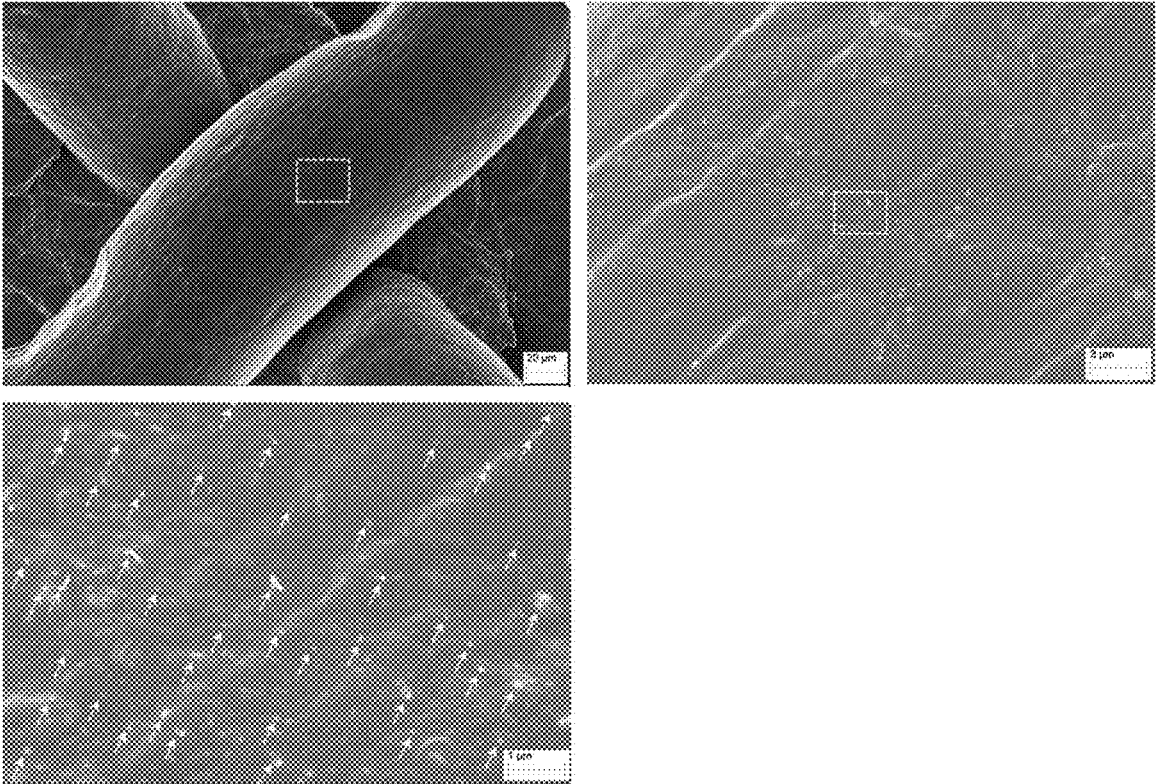
Fig. 12. High resolution SEM images of PDMS/CNT microstructure with CNT clearly observed. From these high resolution SEM images, individual CNT can be observed clearly (as the arrows show).

FIG. 14A
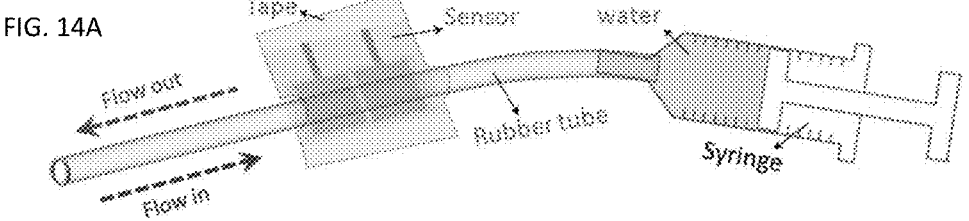
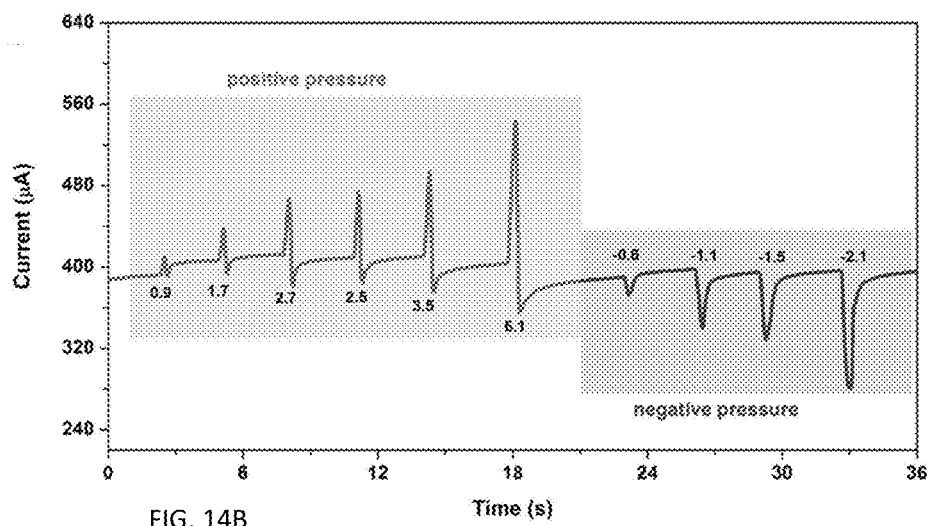
FIG. 14B

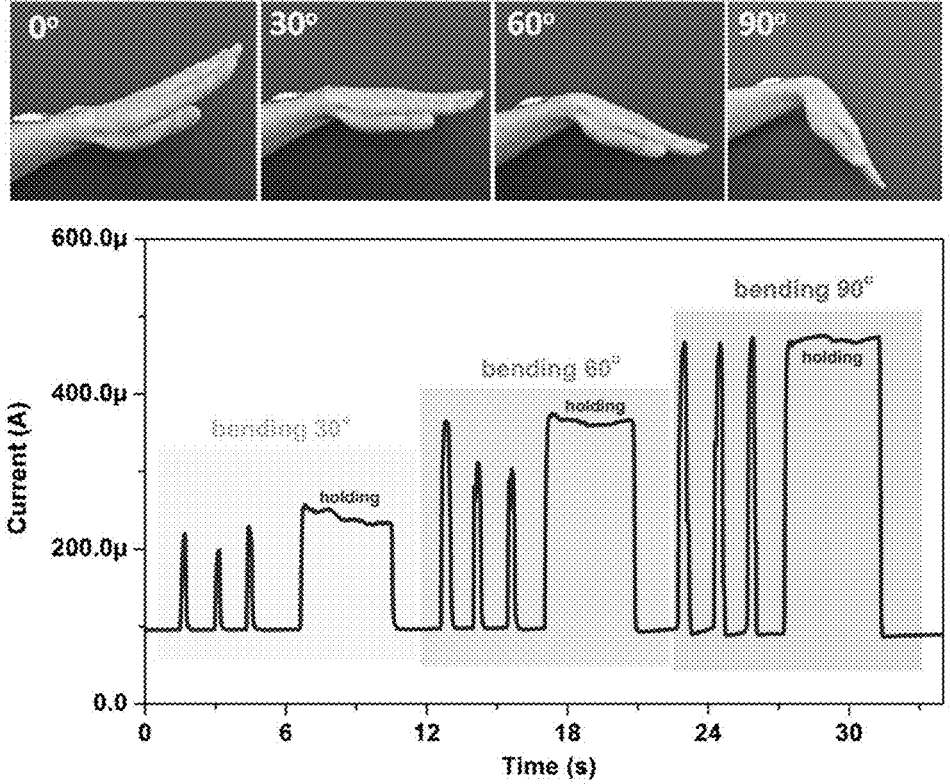
Fig. 15. Application of the pressure sensor for joint bending monitoring.

Screen printed electrode patterns

Patterned conductive microstructure

Flexible pressure sensitive e-skin

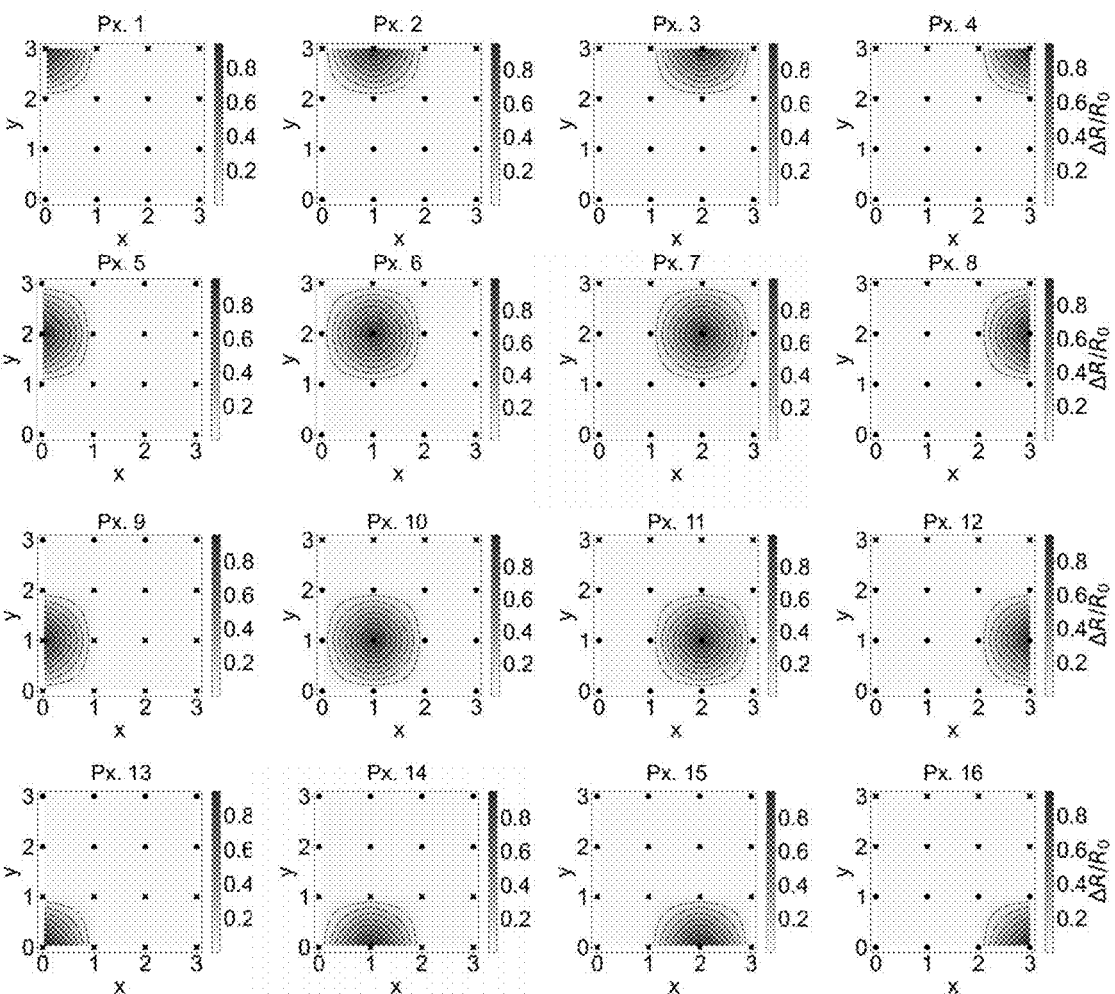
Fig. 17. Verification of the well functioning of all the 16 pixels in the pressure sensitive e-skin by pressing each pixel in sequence.

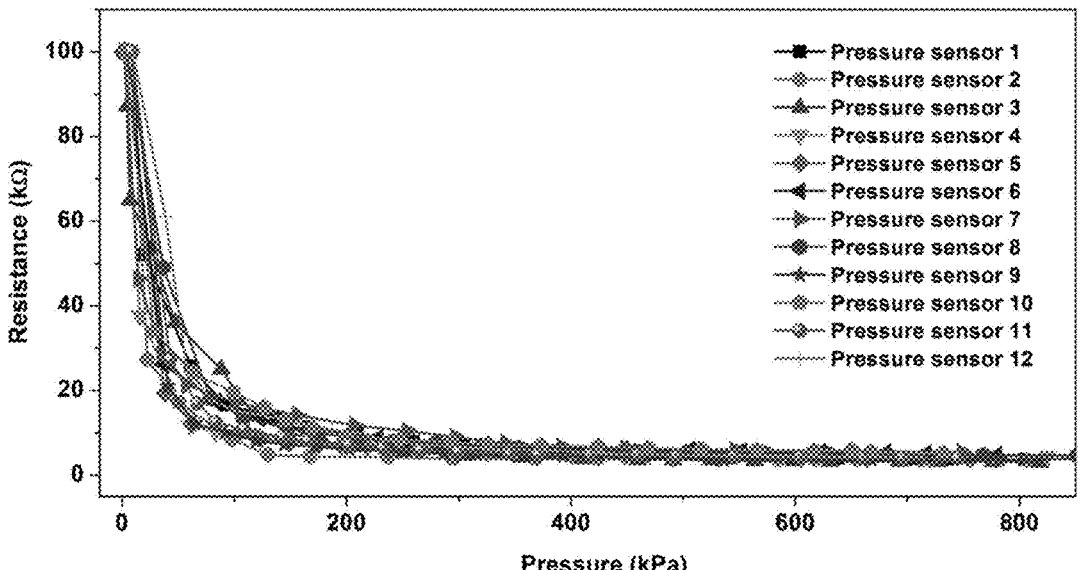
Fig. 18. Calibration of the 12 pressure sensors integrated in the smart insole.

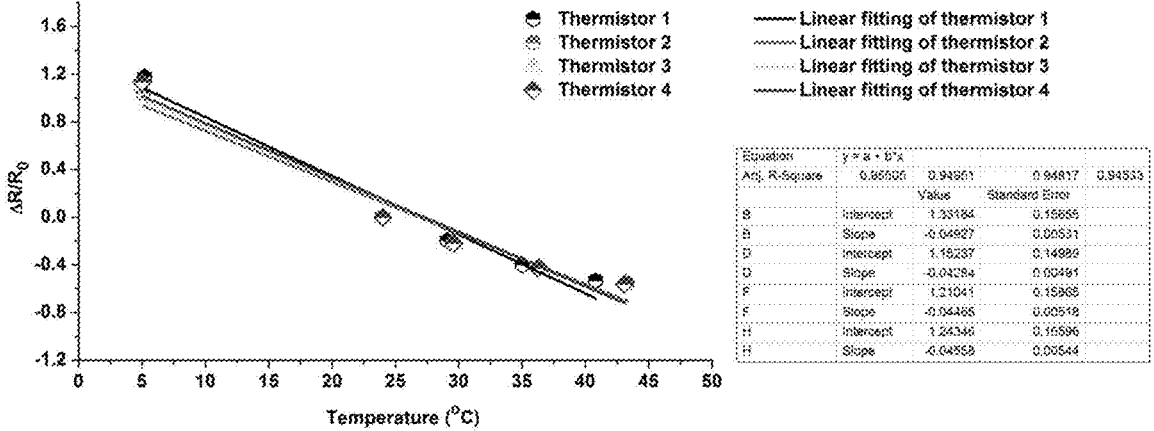
Fig. 19. Calibration of the 4 thermistors integrated in the smart insole.

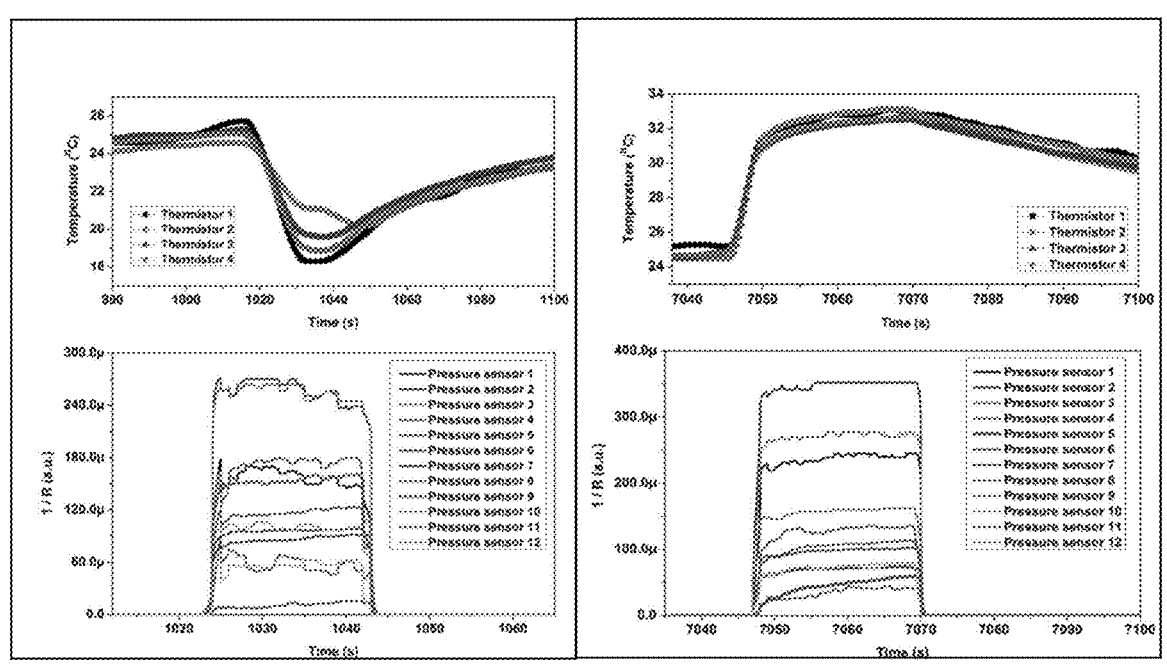
FIG. 20A                    FIG. 20B

FIG. 21:

Table 1. Comparison of pressure sensors presented in this work and other recently reported pressure sensors

| NO. | Sensitivity (kPa$^{-1}$) | Working Range (max. kPa) | Manufactuing Method | Ref. |
|---|---|---|---|---|
| 1 | 0.00017~0.0005 | ~ 1200 | Compact conductive composites | 31 |
| 2 | 1.4 ~ 10.3 | ~ 8 | Periodic micropyramid structure based on silicon mold | 4 |
| 3 | 0.11 ~ 0.76 | ~ 10 | periodic square micropyramids based on silicon mold | 32 |
| 4 | 0.04 ~ 0.3 | ~ 100 | Periodic micropyramid structure based on silicon mold | 6 |
| 5 | 0.87 ~ 2 | ~ 9 | Periodic micropillars based on silicon mold | 24 |
| 6 | 0.79 ~ 1.8 | ~ 1.2 | Regular microstructure molded from silk textile | 1 |
| 7 | 1.14 | ~ 5 | Gold nanowires coated tissue paper | 26 |
| 8 | 0.27 ~ 19.8 | ~ 6 | Random microstructure molded from plant leave | 2 |
| 9 | 0.45 ~ 25.1 | ~ 40 | Random microstructure molded from abrasive paper | 16 |
| 10 | 0.02 ~ 0.05 | ~ 7 | Hydrogel-based pressure sensor | 33 |
| 11 | 0.04 ~ 23.87 | ~ 1000 | Periodic mesh-molded microstructures + printed side-by-side electrodes | This work |

SCALABLE AND HIGH-PERFORMANCE PRESSURE SENSORS FOR WEARABLE ELECTRONICS

CROSS REFERENCE TO RELATED APPLICATIONS

This Patent Application is a continuation of International Patent Application No PCT/US2020/028503, filed on Apr. 16, 2020, which claims priority to U.S. Provisional Patent Application No. 62/835,129, entitled "SCALABLE AND HIGH-PERFORMANCE PRESSURE SENSORS FOR WEARABLE ELECTRONICS," filed Apr. 17, 2019, which are both incorporated herein by reference in their entireties.

SUMMARY

Flexible pressure sensors with high sensitivity, broad working range and good scalability are highly desired for the next-generation of wearable electronic devices. However, manufacturing of such pressure sensors still remains challenging. Embodiments herein provide large-area compliant and cost-effective processes to fabricate high-performance pressure sensors using mesh-molded periodic microstructures and printed side-by-side electrodes. The fabricated pressure sensors advantageously exhibit low operating voltage (e.g., 1 V), high sensitivity (e.g., 23.87 kPa$^{-1}$), low detection limit (e.g., 7.4 Pa), fast response/recovery time (e.g., 25/20 ms), and excellent reliability (e.g., over 10,000 cycles). Additionally, the sensors show broad working range (e.g., 7.4~1,000,000 Pa), high tunability, large-scale production feasibility, and significant advantage in creating sensor arrays with self-defined patterns. The versatility of various device embodiments is demonstrated in various human activity monitoring and spatial pressure mapping as electronic skins. Furthermore, utilizing printing methods, a flexible smart insole with a high level of integration for both foot pressure and temperature mapping is demonstrated.

Wearable human-interactive devices can improve our quality of life and health. Flexible pressure sensors, as an important element of human-interactive devices, are of great interest and have a wide range of applications such as continuous health monitoring, personal diagnostics, robotics, prostheses, and the Internet of Things. Over the past decade, significant advancement has been achieved in fabricating pressure sensors based on resistive, capacitive, transistive, piezoelectric, and triboelectric sensing mechanisms. For a pressure sensor, two components are typically necessary: one or more pressure-sensing layers and conductive electrodes. Variation in electrical properties of the sensing layers under applied pressure is collected and transmitted through the conductive electrodes, thus to transduce external mechanical stimuli into electrical signals.

Introducing microstructures into the pressure-sensing layers is an effective way to achieve enhanced performance in detection limit, sensitivity, response/recovery time, and reproducibility (1-3). Numerous efforts have been made in recent years to construct pressure-sensing microstructures. One of the most investigated strategies is the use of patterned silicon molds to fabricate uniform and periodic microstructures, including micropyramids (4-7), microdomes (3, 8-9), microgrooves (10-11), micropillars (12), and microcubes (13). Silicon molds are usually on wafer-scale and their preparation can be complicated, expensive, and time-consuming, involving traditional lithography and multistep etching processes (1, 2, 14). These drawbacks limit their large-area application despite their effectiveness. Alternative methods for microstructure fabrication have been explored. Silk textile was used as a mold to construct pressure sensitive microstructures, with the working range limited to 1.2 kPa (1). Plant leaves (2, 14, 15) and abrasive papers (16-17) were also employed as templates to prepare pressure-sensing microstructures. However, the size and shape of the microstructures on these templates are randomly distributed with poor uniformity, periodicity and controllability, which make it challenging to fabricate reproducible pressure sensors from batch to batch. Therefore, the significant trade-off between scalability, fabrication cost, and microstructure quality (i.e. regularity, periodicity, and tunability) still remains a big challenge for cost-effective manufacturing of pressure sensors with desirable comprehensive performance.

In certain embodiments, the scalable fabrication of high-quality pressure-sensing microstructures is achieved using a mesh-molding strategy. Screen meshes are widely used for separating particles of different sizes. The micro-patterns of screen meshes are very uniform, periodic, and highly tunable in size and periodicity (FIG. 7). Therefore, screen meshes are useful molds to construct large-area periodic microstructures.

In addition to the sensing layer, the electrode configuration of pressure sensors has a big impact on their performance. Top-bottom electrode configurations are the most reported sensor layouts with three common scenarios: 1) the pressure-sensing layer is sandwiched between two electrodes (18-23); 2) the conductive pressure-sensing microstructure itself is used as an electrode paired with another counter electrode (4, 24-25); and 3) two conductive microstructures are interlocked with each other (1, 8, 9, 12, 16). These out-of-plane electrode configurations are suitable to fabricate a single pressure sensor but are disadvantageous for constructing highly integrated devices that require planar interfaces or low profiles. Recently, interdigitated electrodes were used to fabricate flexible pressure sensors (26-30). Nevertheless, it is difficult to use the interdigitated electrodes to fabricate sensor arrays with high pixel density. Additionally, these interdigitated electrodes are usually prepared via metal deposition techniques with the assistance of shadow masks, which can be time-consuming and not suitable for large-area production. In certain embodiments, a side-by-side electrode configuration is implemented for constructing flexible pressure sensors with high sensitivity and ultra-broad working range. Printing techniques are employed in certain aspects to produce the side-by-side electrodes, which greatly simplifies the fabrication processes and enables high-throughput production of flexible electrodes. Additionally, such a side-by-side electrode configuration enables utilizing printed electrodes to fabricate pressure sensor arrays with well-defined patterns, facilitating high-level integration of multifunctional devices.

Certain embodiments herein provide a large-area compliant and cost-effective strategy to fabricate high-performance pressure sensors via the combination of the mesh-molded pressure-sensing microstructures and printed side-by-side electrodes. In certain aspects, the flexible pressure sensors exhibit high sensitivity (e.g., 23.87 kPa$^{-1}$), low detection limit (e.g., 7.4 Pa), ultra-broad working range (e.g., 7.4~1,000,000 Pa), fast response/recovery (e.g., 25/20 ms), good reliability (e.g., over 10,000 cycles), excellent tunability, and great advantage in creating sensor arrays with self-defined patterns. The performance of the pressure sensors provides a solid platform for monitoring a wide range of human activities as well as resolving spatial distribution and magnitude of external pressure as an electronic skin (e-skin). Moreover, a smart insole is provided with a high level of integration for both foot pressure and temperature mapping, which is promising for foot ulcer prevention/detection, medical diagnostics, and sports applications. The scalable and cost-effective manufacturing along with the good comprehensive performance of the pressure sensors makes them attractive for use in wearable smart devices and human-machine interfaces.

According to certain embodiments, pressure-sensing layers are prepared using a screen mesh molding strategy. Screen meshes are used as the molds and periodic microstructures on the screen mesh molds are transferred to the pressure sensing layer. Screen meshes are pressed into the surface of a soft polymer sheet. Then, the screen meshes are peeled off from the polymer sheet, leaving an inverse mesh microstructure on the polymer template. Next, conductive materials are coated on the inverse microstructured polymer template, followed by casting an elastomer precursor layer on the polymer template. After curing or drying the elastomer precursor, the conductive and microstructured pressure-sensing film is peeled off, or otherwise removed, with the conductive materials embedded in the microstructure surface.

According to an embodiment, a flexible pressure sensor is provided. The flexible pressure sensor includes a first layer including a plurality of pressure-sensitive microstructures, and a second layer including one or more electrode pairs, each of the one or more electrode pairs comprising a first electrode positioned adjacent a second electrode on the second layer.

According to another embodiment, a flexible pressure sensor is provided. The flexible pressure sensor includes a first layer including plurality of pressure-sensitive microstructures, and a second layer including at least one electrode pair, the at least one electrode pair comprising a first electrode and a second electrode, the first and second electrodes positioned on the second layer in a side-by-side configuration.

According to another embodiment, a method of making a flexible pressure sensor is provided. The method includes forming a first layer including a plurality of pressure-sensitive microstructures, and forming a second layer including one or more electrode pairs, each of the one or more electrode pairs comprising a first electrode positioned adjacent a second electrode on the second layer, and attaching the first layer to the second layer.

In certain aspects, the forming the first layer includes forming a polymer template having an inverse mesh structure, forming a conductive microstructured film on the polymer template, and removing the conductive microstructured film from the polymer template, the conductive microstructured film including a conductive material embedded in a silicone material.

In certain aspects, the forming the first layer includes printing a conductive ink pattern on a flexible polymer substrate to form the one or more electrode pairs on the flexible polymer substrate. The printing may include inkjet printing, screen printing, stencil printing, etc.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

4

BRIEF DESCRIPTION OF THE SEVERAL VIEWS OF THE DRAWING(S)

The detailed description is described with reference to the accompanying figures. The use of the same reference numbers in different instances in the description and the figures may indicate similar or identical items.

FIG. 7 shows photographs and optical images of screen meshes with different microstructure sizes.

FIG. 8 shows optical images and surface profiles of the reversed microstructures created on PS templates after peeling of the screen meshes with different microstructure sizes (60, 100 and 200 mesh count, respectively).

FIG. 9 shows optical images and surface profiles of PDMS microstructures molded from different screen meshes (60, 100 and 200 mesh count, respectively).

FIGS. 10A-10C shows a cross-sectional image (FIG. 10A), a schematic illustration (FIG. 10B) and robustness evaluation (FIG. 10C) of the conductive CNT network imbedded in the surface of PDMS microstructures according to an embodiment.

FIG. 11 shows SEM images of conductive PDMS/CNT microstructures molded from different screen meshes (60, 100 and 200 mesh count, respectively).

FIG. 12 shows high resolution SEM images of a PDMS/CNT microstructure with CNT clearly observed.

FIG. 14A shows a schematic illustration of a sensitive pressure sensor in monitoring the pressure of an artificial vessel.

FIG. 14B shows a response behavior of the sensitive pressure sensor in monitoring the pressure of an artificial vessel.

FIG. 15 shows application and response signals of a pressure sensor embodiment for joint bending monitoring.

FIG. 17 shows a verification of the well functioning of all the 16 pixels in a pressure sensitive e-skin, according to an embodiment, by pressing each pixel in sequence.

FIG. 18 shows calibration of 12 pressure sensors integrated in the smart insole according to an embodiment.

FIG. 19 shows calibration of 4 thermistors integrated in the smart insole according to an embodiment.

FIG. 20A shows recorded response curves of the 4 printed thermistors and the 12 pressure sensors when a cold foot (e.g., foot immersed into cold water of 15° C. for a while and quickly dried with a towel) steps on the smart insole for about 20 seconds and then is taken off from the smart insole.

FIG. 20B shows recorded response curves of the 4 printed thermistors and the 12 pressure sensors when a hot foot (e.g., foot immersed into hot water of 45° C. for a while and quickly dried with a towel) steps on the smart insole for about 20 seconds and then is taken off from the smart insole.

FIG. 21 illustrates Table 1 which shows a comparison of pressure sensors according to the present embodiments and prior reported pressure sensors.

DETAILED DESCRIPTION

Pressure Sensor Design

Figures 1A, 1B, 1C, 1D, 1E:
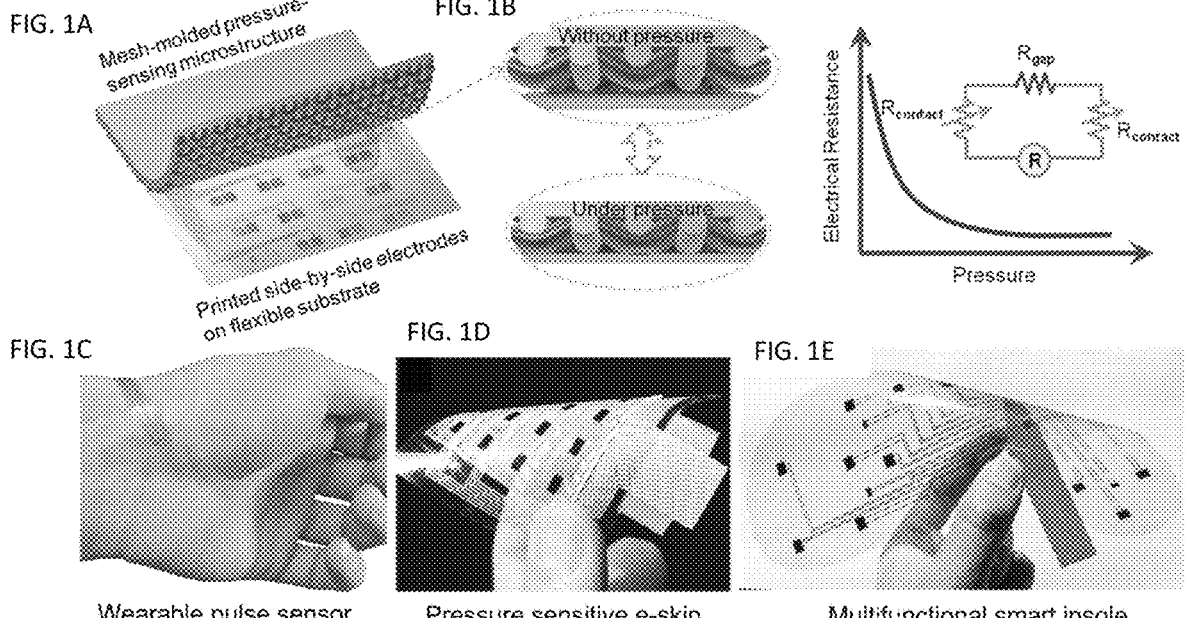
FIG. 1A illustrates a pressure sensor design according to an embodiment.
FIG. 1B illustrates a pressure sensor design including a side-by-side electrode configuration according to an embodiment.
FIGS. 1C-1E show photographs showing the broad application range of the pressure sensors of the present embodiments, including a wearable pulse sensor (FIG. 1C), a flexible pressure sensitive e-skin (FIG. 1D), and a flexible smart insole with a high level of integration for simultaneous mapping of foot pressure and temperature (FIG. 1E).

FIG. 1A illustrates a pressure sensor design according to an embodiment. In this embodiment, the pressure sensor include two components: 1) periodic pressure-sensing microstructures, and 2) flexible side-by-side electrodes. In certain embodiments, the flexible electrodes are prepared using printing techniques, which allow for fabricating reproducible electrodes with well-defined patterns. Unlike most of the reported pressure sensors with top-bottom electrodes, embodiments herein provide a side-by-side electrode configuration (see, e.g., FIG. 1B), which facilitates incorporating printed electrodes into pressure sensors and creating sensor arrays with self-defined patterns. The side-by-side electrode configuration also advantageously exhibits higher sensitivity and broader working range when compared to top-bottom electrodes, as discussed below. The operating principle of these pressure sensor embodiments is based on a variation in contact resistance between the conductive microstructure and each of the two electrodes (see, FIG. 1B). When pressed, the electrical resistance between the electrodes decreases, and this change in resistance is recorded using an external circuitry.

In an embodiment, the periodic pressure-sensing microstructures are fabricated via a mesh-molding method. Compared with microstructures based on expensive silicon molds and other templates with random structures (e.g. plant leaf, textile, paper, etc.), the microstructures fabricated through the present scalable mesh-molding method embodiments are very uniform, periodic, and highly tunable, e.g., from tens of micrometers to thousands of micrometers. Combination of such highly tunable microstructures and the side-by-side electrodes allows for manufacturing pressure sensors or self-defined sensor arrays with high sensitivity and broad working range from small (e.g., 7.4 Pa) to large (e.g., 1,000,000 Pa) pressure monitoring, exhibiting good potential for fabricating versatile human-machine interfaces, as presented in FIGS. 1C-E.

Scalable Fabrication of Periodic Pressure-Sensing Microstructures

Figures 2A, 2B, 2C, 2D, 2E, 2F, 2G:
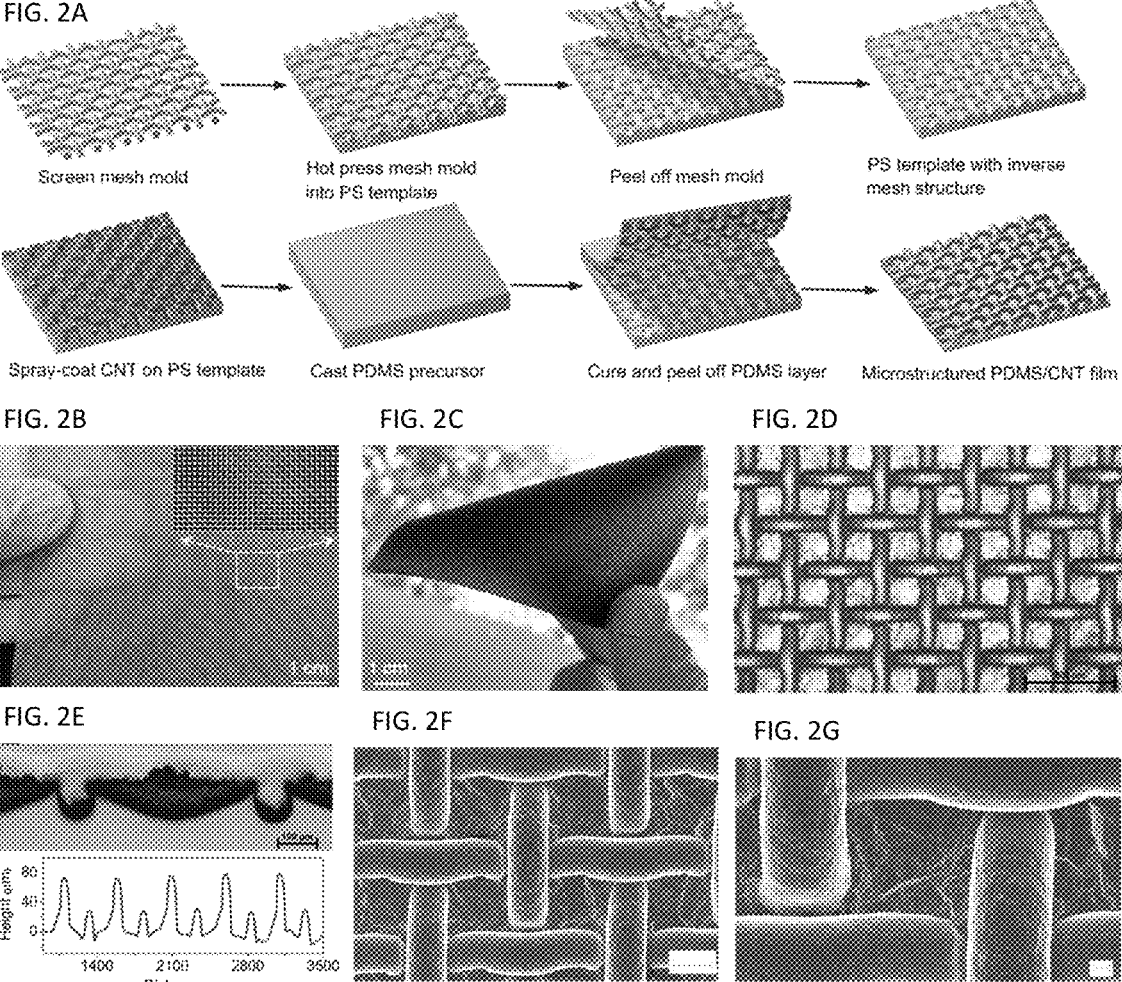
FIG. 2A shows a fabrication process for producing pressure-sensing microstructures via mesh-molding according to an embodiment.
FIG. 2B shows a photograph of a stainless-steel screen mesh, which may be used as a mold.
FIG. 2C shows a picture of the as-prepared conductive PDMS/CNT microstructured film.
FIG. 2D shows an optical micrograph of PDMS microstructure molded from a screen mesh.
FIG. 2E shows a cross-sectional image of a sliced PDMS/CNT microstructure according to an embodiment.
FIG. 2F and FIG. 2G show SEM images of the PDMS/CNT microstructure with different magnification.

FIG. 2A shows a fabrication process for producing pressure-sensing microstructures via mesh-molding according to an embodiment. In this embodiment, a piece of pre-cleaned screen mesh (FIG. 2B) is hot-pressed into the surface of a polymer, e.g., polystyrene (PS), sheet. After cooling down, the screen mesh is peeled off from the polymer sheet, leaving an inverse mesh microstructure on the polymer template (see, FIG. 8). Next, a conductive microstructured film is formed on the inverse microstructured polymer template. For example, in an embodiment, a conductive material layer, e.g., a conductive carbon nanotube (CNT) layer, is uniformly applied, e.g., spray-coated, on the inverse microstructured polymer template, followed by casting a siloxane, e.g., polydimethylsiloxane (PDMS), precursor layer. After curing the PDMS, the conductive and microstructured PDMS/CNT film (FIG. 2C) is peeled off, with a robust CNT network embedded in the microstructured surface (FIG. 2E). Other useful conductive materials include silver flake or powder, graphene, silver nanowires, carbon black, short carbon fibers, etc. Other useful elastomer materials include polyurethane, natural or synthetic rubbers and other types of silicone rubbers.

Figure 10C:
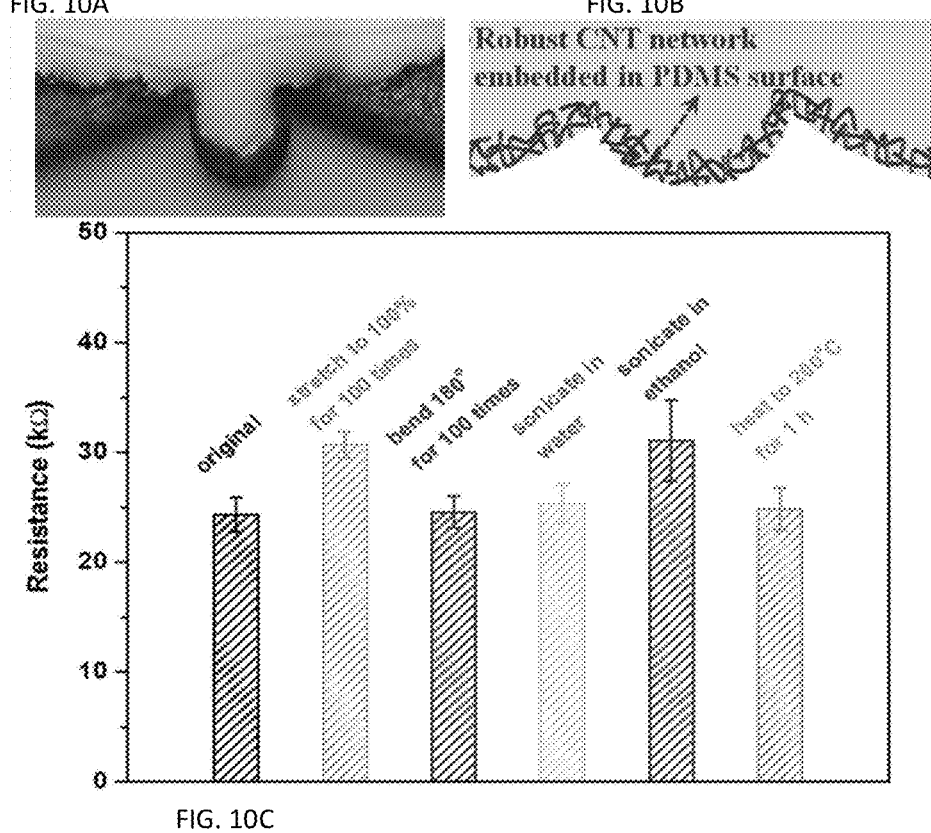

The microstructured PDMS film has a similar topography as the screen meshes, as shown in the optical images (FIG. 2D, FIG. 9). These mesh-molded microstructures are very uniform, periodic, and highly tunable by using different meshes as molds. FIG. 2E shows the cross-sectional image of a sliced PDMS/CNT microstructure; the conductive CNT layer is firmly embedded in rather than attached to the PDMS microstructure surface, which can greatly improve the robustness of the conductive microstructures as verified in FIG. 10B. From the surface profile (FIG. 2E), regular and periodic micro-patterns with ≈75 and ≈27 μm height are alternately observed, corresponding to alternately woven microfibers of the screen mesh mold. Scanning electron microscopy (SEM) images in FIGS. 2F-2G and FIG. 11 show more clearly the morphology of the PDMS/CNT microstructures, which are very similar to the topography of screen meshes. In the high-resolution SEM images (FIG. 12), a single CNT could also be observed on the PDMS/CNT microstructure. This microstructure fabrication strategy achieves a good balance between fabrication cost, scalability and microstructure quality (i.e. uniformity, regularity, and periodicity). Moreover, this method shows excellent microstructural tunability from tens of micrometers to thousands of micrometers, widely broadening their application range in manufacturing pressure sensors for different purposes.

Printed Side-by-Side Electrodes for Improved Sensitivity and Working Range

Figures 3A, 3B, 3C, 3D, 3E, 3F, 3G, 3H, 3I:
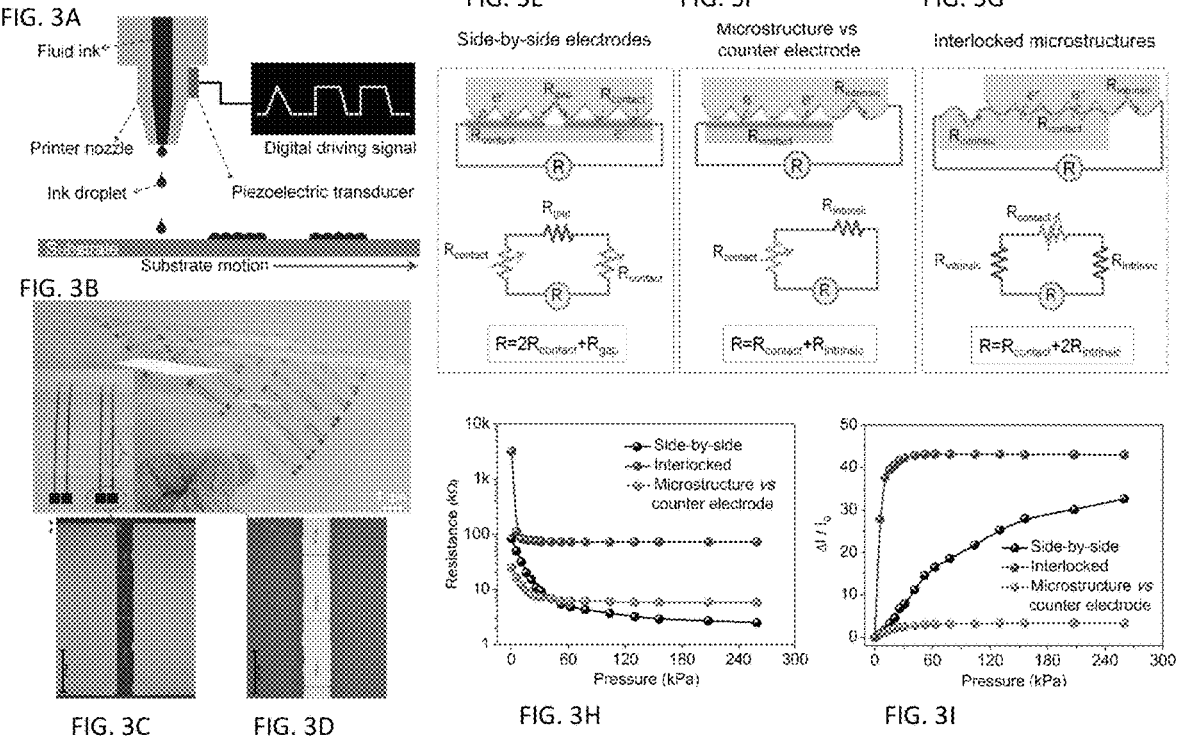
FIG. 3A shows the working principle of inkjet printing.
FIG. 3B shows conductive electrode patterns.
FIGS. 3C-3D show optical microscope images of continuous silver pads with ≈197 μm gaps and ≈312 μm trace lines printed on a flexible PEN substrate.
FIGS. 3E-3G show the pressure sensing behaviors of three different electrode configurations, the side-by-side electrodes (FIG. 3E), microstructure vs counter electrode (FIG. 3F), and interlocked conductive microstructures (FIG. 3G).
FIGS. 3H-3I show a comparison in response behaviors of pressure sensors with three electrode configurations: side-by-side electrodes, microstructure vs counter electrode, and interlocked microstructures.

Printing techniques show good potential for producing flexible electronics through cost-effective and high through-put processes. In certain embodiments, printed side-by-side electrodes (for scalable manufacturing of pressure sensors) are combined with the mesh-molded pressure-sensing microstructures. In an embodiment, inkjet printing is used to fabricate the side-by-side electrodes on a flexible substrate. Inkjet printing is a non-contact, digital, and additive printing method with minimal waste of materials (FIG. 3A). Additionally, inkjet printing allows for changing the layout design easily and rapidly. For the electrode design, a small gap, e.g., of 200 μm, is set between the side-by-side electrodes (e.g., 2 mm×2 mm) with a trace line, e.g., of 300 μm. A conductive ink, e.g., silver ink, is inkjet printed on a planarized polymer substrate, e.g., a 125 μm thick planarized polyethylene naphthalate (PEN) substrate. After drying and sintering, flexible and highly conductive electrode patterns can be obtained, as shown in FIG. 3B. The optical microscope images of FIGS. 3C-D show continuous silver pads with ≈197 μm gaps and ≈312 μm trace lines printed on the flexible PEN substrate.

Next, the pressure sensing behaviors of three different electrode configurations, the side-by-side electrodes (FIG. 3E), microstructure vs counter electrode (FIG. 3F), and interlocked conductive microstructures (FIG. 3G), are compared. The pressure sensor with the interlocked conductive microstructures shows high sensitivity initially but the working range is very narrow (limited to 50 kPa), as indicated in FIGS. 3H-3I. Pressure sensors based on this configuration are suitable for detecting small pressure, but cannot be used to detect relatively large pressure. For the side-by-side electrode and microstructure vs counter electrode configurations, the former advantageously shows more dramatic resistance variation (FIG. 3H) and much higher sensitivity (FIG. 3I). This is because there are two contact resistors ($R_{contact}$, which play a dominant role in the whole circuit) in the side-by-side electrode circuit while there is only one $R_{contact}$ in the microstructure vs counter electrode circuit, as depicted in the schematic resistance models (FIGS. 3E-3F). A detailed discussion regarding the electrode configurations is provided below. Overall, the side-by-side electrodes advantageously show higher sensitivity and broader working range compared to the microstructure vs counter electrode and interlocked microstructures. Moreover, the sideby-side electrodes are printable, which allows scalable manufacturing of pressure sensors with desirable performance.

Electromechanical Response of the Pressure Sensors

Figures 4A, 4B, 4C, 4D, 4E, 4F, 4G, 4H:
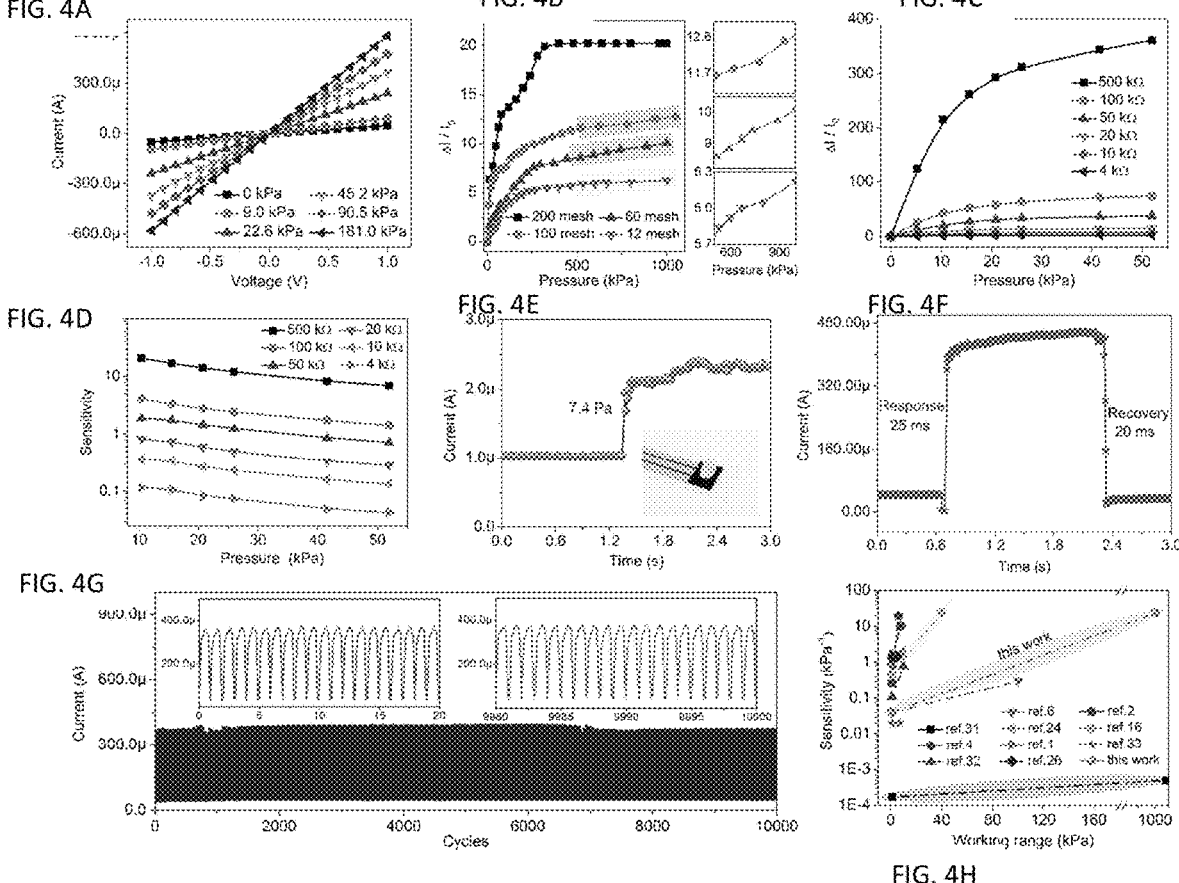
FIGS. 4A-4H show electromechanical characteristics of pressure sensors according to certain device embodiments.

The electromechanical characteristics of the pressure sensors according to certain device embodiments are shown in FIGS. 4A-4H. The linear behavior of the I-V curves in FIG. 4A indicates that the devices follow Ohm's law and the resistance decreases under pressure. For the other results, a constant voltage of 1 V is applied to the devices. FIG. 4B shows the sensing behaviors of pressure sensors with different mesh microstructures. Pressure sensors with larger microstructures exhibit relatively lower sensitivity but a wider working range. It is observed that pressure sensors with microstructures of 100, 60, and 12 mesh count can detect pressure as high as 1000 kPa. Such a broad working range is rarely achieved for microstructure-based pressure sensors. Moreover, the initial resistance of the sensors could be easily tuned from several kilo-ohms to hundreds of mega-ohms (e.g., ≈5 orders of magnitude) by adjusting the tightness between the top conductive microstructure and the bottom electrodes. Thus, the pressure-sensing behaviors (FIG. 4C) and sensitivity (FIG. 4D, defined as the relative current change in response to pressure change, i.e. $(\Delta I/I_0)/\Delta P$) of the pressure sensors are also highly tunable by regulating the initial resistance. For some applications (e.g. subtle physiological signal detection), high sensitivity is necessary for good signal recognition. In contrast, for certain applications (e.g. foot pressure monitoring), low sensitivity but high pressure detecting capability are needed for stable signal output. Notably, the present pressure sensor embodiments meet these requirements readily, e.g., by tuning the microstructure size as well as the initial resistance to obtain a desirable sensitivity and working range.

The lowest detection limit of the pressure sensor embodiments was evaluated. As shown in FIG. 4E, upon loading a grain of rice (24 mg, corresponding to 7.4 Pa) on a sensor, an obvious increase in current could be observed, indicating a very low detection limit. Additionally, the pressure sensor displays an instantaneous response to both loading and unloading of external pressure (FIG. 4F), showing a short response time of ≈25 ms and a recovery time of ≈20 ms. Furthermore, the devices also exhibit excellent durability and reliability when repeatedly loading/unloading a high pressure of 140 kPa for 10,000 cycles at a frequency of 1 Hz (FIG. 4G). Based on the performance mentioned above, the present pressure sensors were compared with other recently reported pressure sensors, as presented in FIG. 4H and Table 1 (FIG. 21). The present pressure sensors show comparable performance in terms of detection limit, response/recovery speed and reliability, but exhibit much superior performance in working range (up to 1000 kPa), sensitivity (0.04 kPa$^{-1}$ to 23.87 kPa$^{-1}$) as well as sensor tunability. Together with the superior scalability and cost-efficiency, such pressure sensors are advantageous and competitive for practical applications.

Various Human Activities Monitoring and Spatial Pressure Mapping

Figures 5A, 5B, 5C, 5D, 5E, 5F, 5G, 5H, 5I, 5J, 5K:
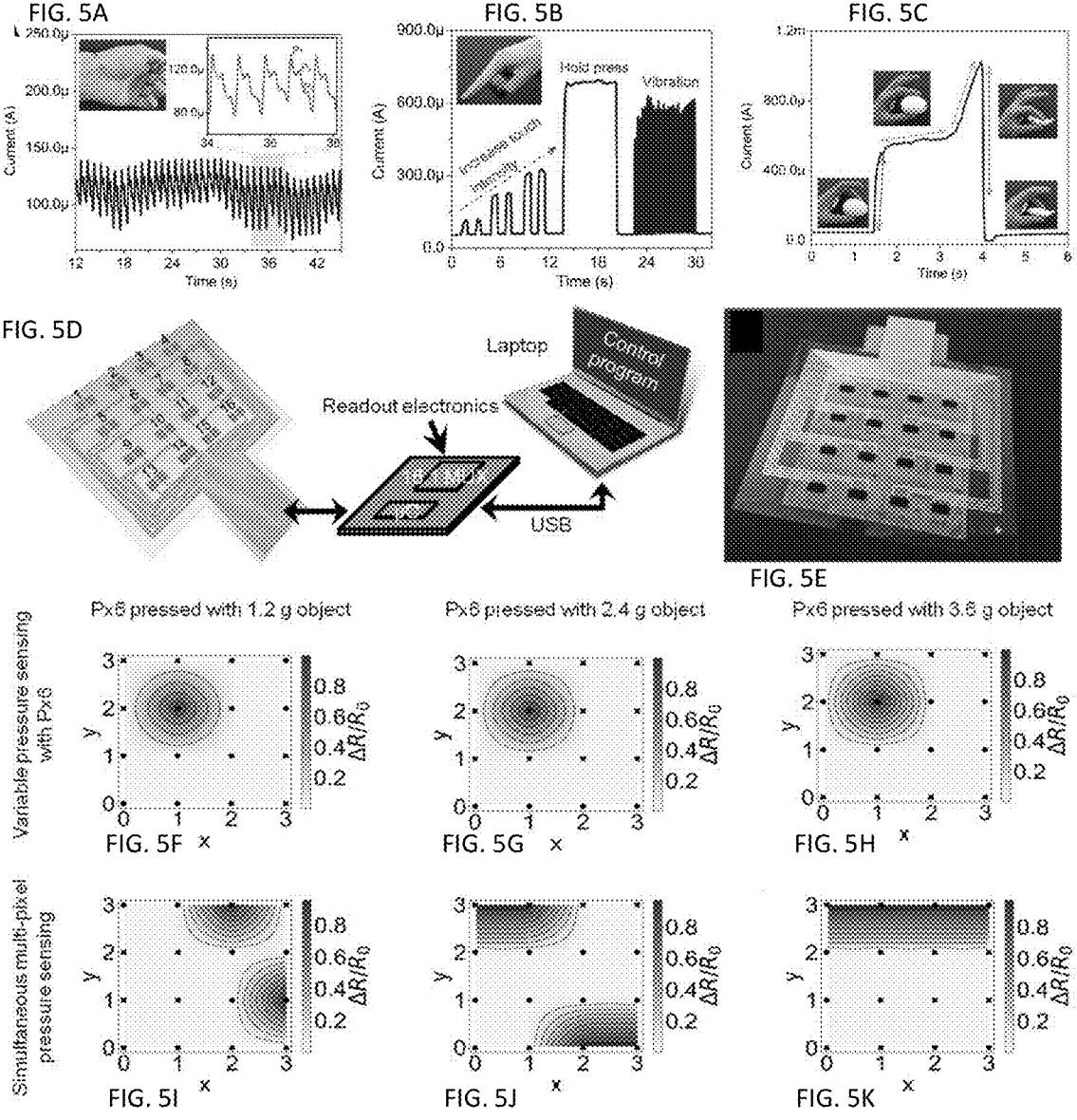
FIGS. 5A-5K shows applications for various human activity monitoring and spatial pressure of pressure sensors according to certain device embodiments.
Figures 13A, 13B, 13C, 13D, 13E, 13F, 13G:
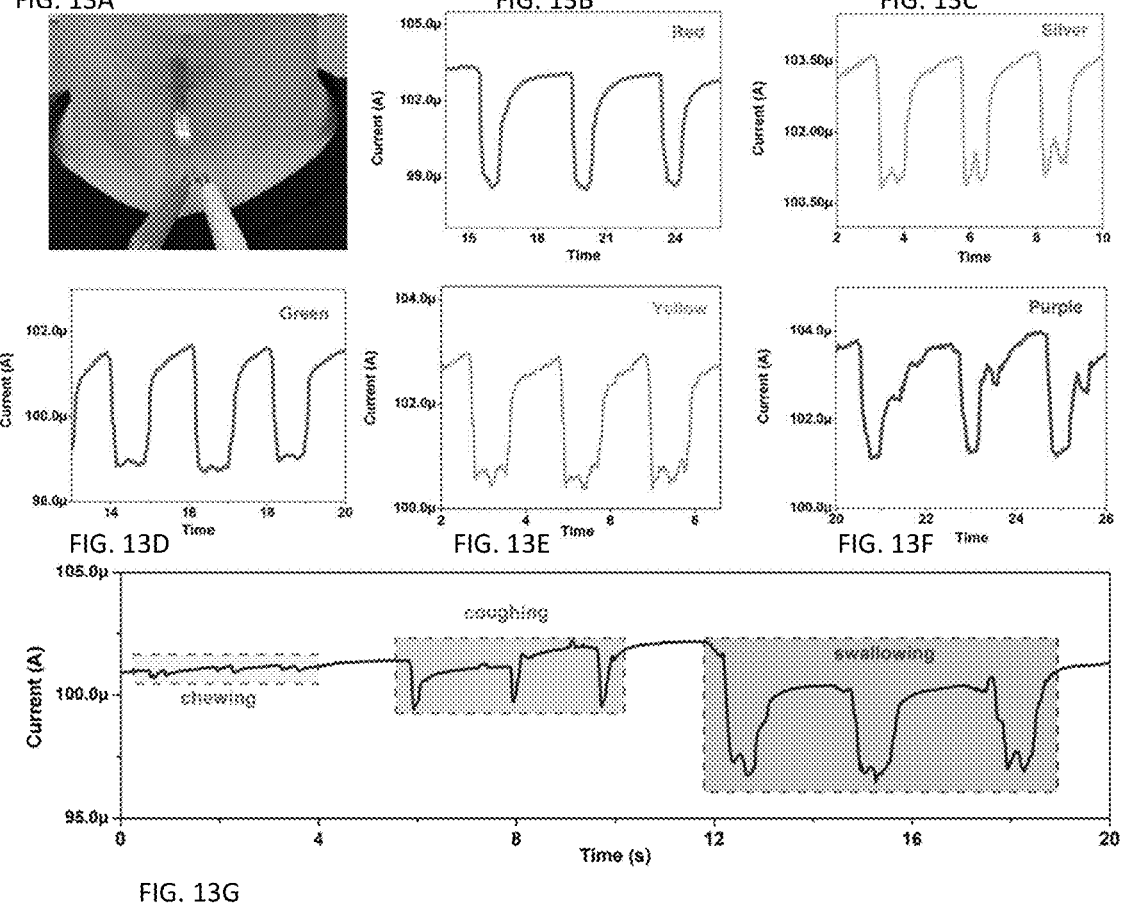
FIGS. 13A-13G shows application and signal patterns of flexible pressure sensors for tiny physiological activity detection, such as speech recognition, chewing, coughing and swallowing monitoring.

Due to the low detection limit and broad working range, flexible pressure sensor embodiments are capable of monitoring both small and large human physiological activities. To explore their practical applications, a pressure sensor was attached to the wrist of a healthy subject (27-year-old male) to record the artery pulse signal. As shown in FIG. 5A, the wrist pulse could be read out accurately from the time-dependent current signals with a periodicity of 73 beats/min. A typical artery pulse waveform consists of three distinguishable peaks, i.e. $P_1$, $P_2$, and $P_3$, as shown clearly in the inset of FIG. 5A. Other subtle physiological signals (e.g. pronouncing, coughing, swallowing, etc) can also be monitored with the present pressure sensors (FIGS. 13A-G). With the merits of low detection limit and high sensitivity, the present pressure sensors can be used to detect and monitor tiny human physiological activities. First, the capability of the present sensors in detecting the delicate muscle motions of the vocal cords during pronunciation was evaluated. A pressure sensor was attached onto the throat of a healthy subject, as shown in FIG. 13A. When the subject pronounces different words (e.g. red, silver, green, yellow, purple, ect), the pressure sensors generate distinct signal patterns relating to the pronunciation of the words, as exhibited in FIGS. 13B-F. When one word is repeated, similar signal patterns are recorded, indicating the good reliability of the sensor. In addition, the pressure sensor attached on the throat could also detect other small-scale physiological activities. As shown in FIG. 13G, when the subject chewed, coughed, and swallowed, the pressure sensors also generated different and repeatable signal patterns. These results reveal the potential application of the sensitive pressure sensors in constructing speech recognition devices and wearable healthcare electronics.

Additionally, the present pressure sensors can be used to "feel" human touch. As shown in FIG. 5B, both static press with different intensity and dynamic vibration could be detected in real-time. Moreover, a pressure sensor was employed to continuously monitor the pressure variation during grasping and crushing an egg shell. Based on the recorded signal (FIG. 5C), the whole process could be divided into four stages, including touching, holding, squeezing, and breaking, respectively. Additionally, the potential applications of the devices for monitoring the pressure of an artificial vessel (FIGS. 14A-B) and joint bending motions (FIG. 15) was demonstrated. The flexible and sensitive pressure sensors are also applied to an artificial cardiac system. As shown in FIG. 14A, a soft rubber tube is used as a blood-vessel model due to its similar mechanical properties to real blood-vessel. A flexible pressure sensor is attached onto the artificial blood-vessel with a medical tape, thus to monitor the vessel expansion or contract. Then, a syringe is used as the artificial heart model, which can pump out and pump in water (used as artificial blood). The recorded pressure variation when pumping out and pumping in liquid is shown in FIG. 14B. When liquid is pumped out by the syringe, positive pressure signal is detected due to expansion of the artificial vessel. Notably, the magnitude of the pressure signal is in good consistence with the liquid volume pumped out by the syringe. In contrast, when the liquid is pumped in, negative pressure signal, which also shows good consistence with the liquid volume pumped in, is detected due to contract of the artificial vessel. To evaluate the ability of the flexible sensors in detecting large-scale human motions, a pressure sensor was attached on the finger joint part of a subject and the subject conducted finger bending—release motions with different bending angles (30°, 60°, and 90°, respectively), as shown in FIG. 15. It was observed that the pressure sensor gives different responsive signals to different finger bending motions. Larger bending-release motions cause higher intensity of the recorded signal, revealing potential application for fabricating smart prosthetics and robotics. These results provide the evidence that the present flexible and wearable pressure sensors are adequate for dynamic interaction between a machine and human and may be used for manufacturing wearable diagnostic devices, service robots, artificial limbs, and other smart systems.

Figures 16A, 16B, 16C:
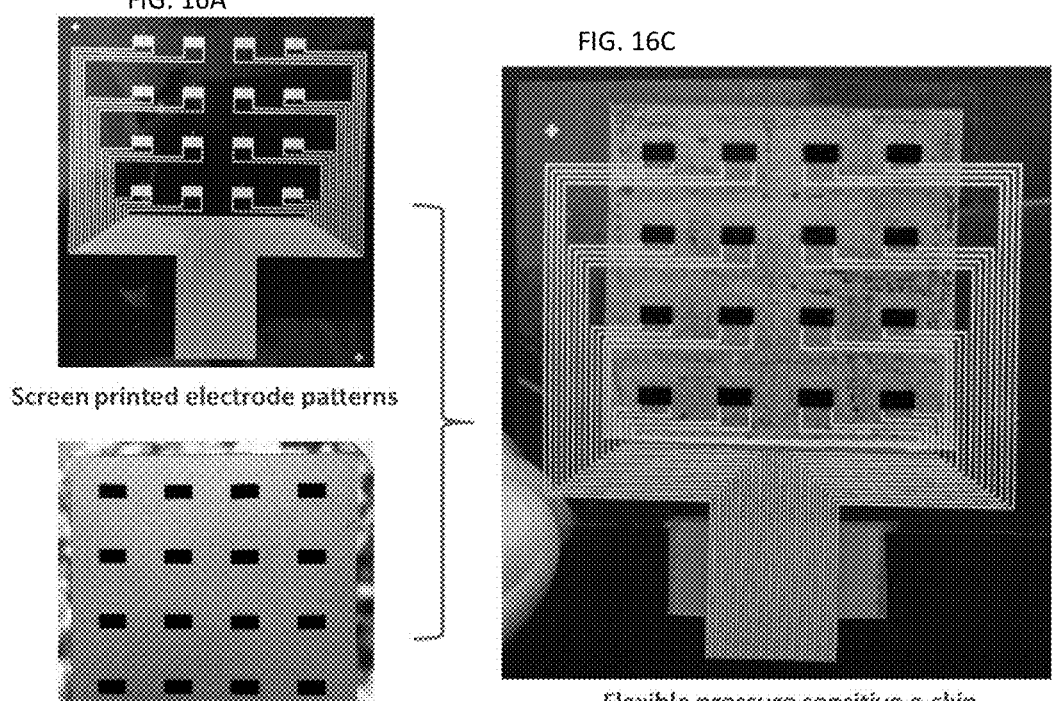
FIG. 16A shows a photograph showing the screen printed silver electrode patterns.
FIG. 16B shows a photograph showing a PDMS/CNT microstructure film with patterned conductive area.
FIG. 16C shows a photograph showing, after assembly of the two components shown in FIG. 16A and FIG. 16B, a flexible pressure sensitive e-skin according to an embodiment.

According to an embodiment, a pressure sensitive e-skin with 4×4 pixels was produced via a combination of printed silver electrodes and a patterned conductive microstructure. A piece of e-skin (FIG. 5E) may be assembled by attaching the patterned conductive microstructure onto the printed electrodes (FIG. 16C). To realize spatial pressure mapping in real-time, the e-skin is connected to a custom data acquisition circuit board with 16 measurement channels (as illustrated in FIG. 5D), which communicates with a computer. A continuous mapping of the resistance change can be reconstructed on the computer. The functionality of every pixel in this e-skin (FIG. 17) was verified. Then, different pressure was applied on a randomly selected pixel (pixel 6 as an example) by placing objects with ≈1.2 g, ≈2.4 g, and ≈3.6 g, respectively. As shown in the reconstructed color mapping (FIGS. 5F-H), the e-skin can distinguish the difference in magnitude of the applied pressure. The capability of the e-skin to resolve spatial pressure distribution was also evaluated by placing two batteries on pixel 3 and 12. The spatial resistance variation is consistent with the battery location, as shown in FIG. 5I. Next, two fingers were pressed on region A (with pixels of 1, 2, 15, and 16) and region B (with pixels of 1, 2, 3, and 4), respectively. The reconstructed color mappings are also in good correlation with the pressure distribution (FIG. 5J-K). These results demonstrate the good capability of the e-skin to resolve spatial distribution as well as the magnitude of the applied pressure.

Smart Insole for Simultaneous Mapping of Foot Pressure and Temperature

Our feet provide the primary interactive surface with the environment during locomotion. Hence, foot health is of great significance to our well-being. Recently, smart insoles for foot pressure detection (3, 16, 34-35) have been reported, which provide feasible solutions for footwear design, sports performance analysis, and injury prevention. Except for foot pressure, foot temperature is also crucial to our health, as foot temperature is a good indicator for our blood circulation condition and can also affect the blood circulation process in our body. Additionally, for diabetes patients who are at risk of developing a foot ulcer, there is an increase in foot temperature before the foot ulcer develops due to inflammation and enzymatic autolysis of the tissue (36). Therefore, monitoring of foot temperature is of great importance for early disease recognition and foot ulcer prevention. Based on these aspects, integration of foot temperature monitoring and foot pressure mapping into a single smart insole through compatible manufacturing process could greatly extend the insole's functions and versatility, which, however, has not been reported in the literature.

Figures 6A, 6B, 6C, 6D, 6E, 6F, 6G, 6H, 6I:
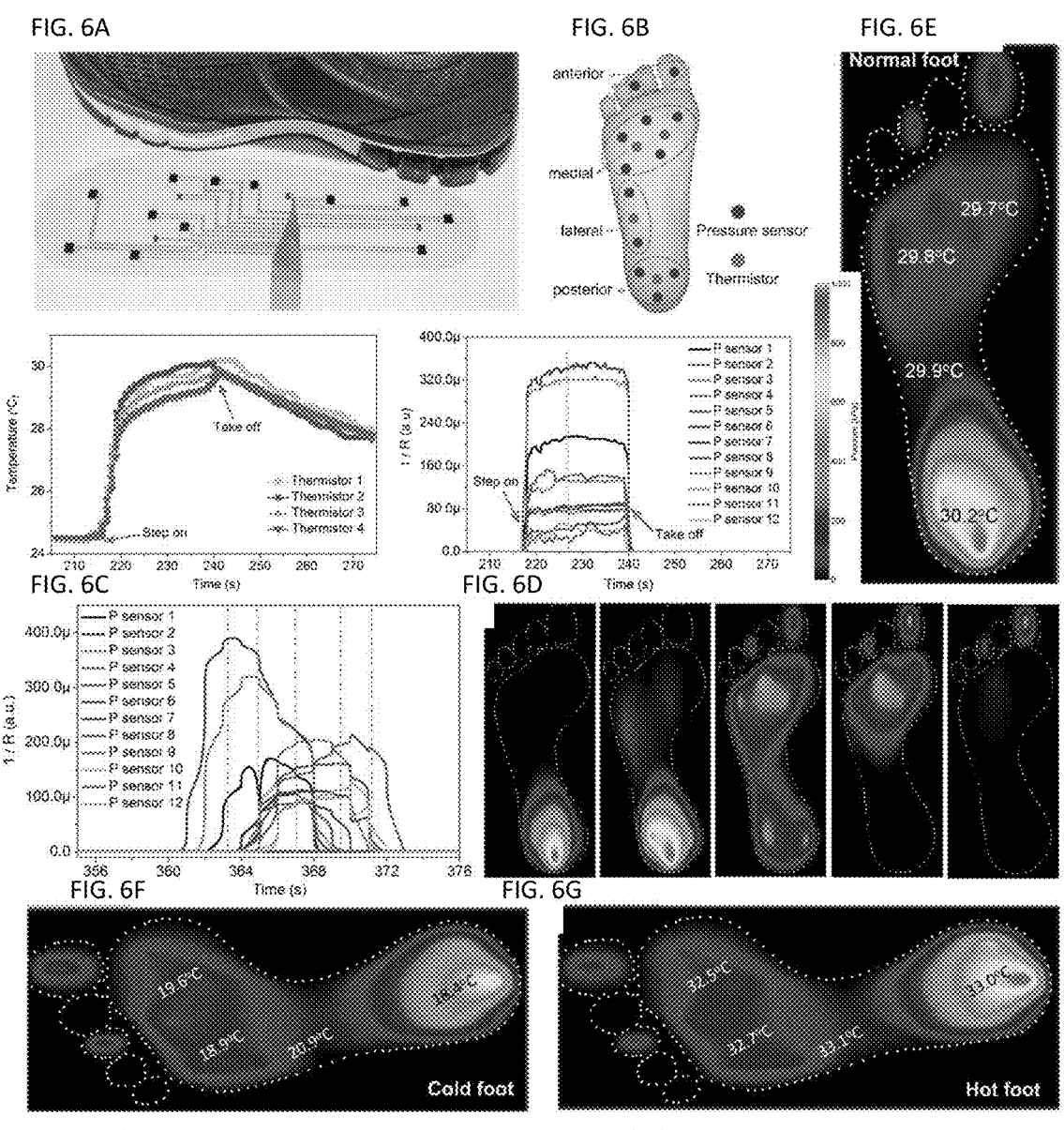
FIG. 6A shows a fabricated smart insole with 12 pressure sensors and 4 printed thermistors according to an embodiment.
FIG. 6B shows the 12 pressure sensors placed at anterior, medial, lateral, and posterior regions, respectively.
FIGS. 6C-6D show recorded response signals of the 4 thermistors and the 12 pressure sensors (P sensor) when a normal foot is stepped on and then taken off from the smart insole.
FIG. 6E shows the reconstructed foot pressure and temperature distribution of the foot.
FIG. 6F shows continuously recorded signal variations of the 12 pressure sensors with a foot walking on the smart insole.
FIG. 6G shows evolution of the extracted foot pressure mapping during the walking process.
FIG. 6H shows the reconstructed foot pressure mapping and temperature distribution of a cold foot.
FIG. 6I shows the reconstructed foot pressure mapping and temperature distribution of a hot foot.

According to an embodiment, a flexible smart insole is provided for both foot pressure and temperature monitoring simultaneously via a scalable and low-cost fabrication process. FIG. 6A shows a fabricated smart insole according to an embodiment. The smart insole includes 12 pressure sensors and 4 printed thermistors (i.e. temperature sensors). As illustrated in FIG. 6B, the 12 pressure sensors are placed at anterior, medial, lateral, and posterior regions, respectively, according to gait kinetics as well as normal and pathological foot anatomy (37). The 4 thermistors are distributed at medial, lateral, and posterior regions thus to monitor the temperature at different foot positions. In an embodiment, the smart insole is fabricated through three steps: 1) inkjet printing electrode patterns on a flexible substrate, 2) stencil printing the thermistors, and 3) installing the pressure-sensing layers and encapsulating the insole, e.g., with a Kapton tape film. The resultant smart insole may be connected to a data acquisition circuit board as mentioned above to record pressure as well as temperature signals in real-time. The calibration process for the pressure sensors and thermistors is described in FIG. 18 and FIG. 19. The calibration of the 12 pressure sensors (FIG. 18) is conducted by measuring the resistance of each sensor under different pressure. Then, plots of resistance versus applied pressure are obtained. Based on these calibration curves, the recorded resistance values may be converted into foot pressure values and reconstruct the plantar pressure maps. The calibration of the thermistors (FIG. 19) is conducted by measuring the resistance of each thermistor at different temperature. Then, linear plots of relative resistance change ($\Delta R/R0$) versus temperature are obtained. This linear characteristic is in good consistence with the behavior of thermistors reported in the literature. These linear curves allow for converting the recorded resistance signal into temperature.

As shown in FIG. 6C, when a person steps on the smart insole, the measured temperature rises from 24.5° C. in the beginning and gradually increases to ≈29.9° C., which is the normal skin temperature of the foot (38). With the foot taken off from the insole, the temperature goes back to the original value slowly. On the other hand, as shown in FIG. 6D, the signals of the 12 pressure sensors exhibit prompt increase and decrease when the foot is placed on and taken off from the insole, respectively, and stay relatively stable when the foot is stepped on the insole. Foot pressure mapping and temperature distribution can be reconstructed from the acquired signals, as shown in FIG. 6E. It is noted that the highest pressure is detected at the posterior region. Medium pressure is distributed at the anterior and medial parts, and low pressure is applied on the lateral area. Such foot pressure distribution is consistent with the results reported in the literature (3, 37). Moreover, during the dynamic walking process, signals variation of the 12 pressure sensors could also be recorded continuously, as given in FIG. 6F. Based on these continuous signals, the evolution of foot pressure mapping can be reconstructed as shown in FIG. 6G. Such foot pressure evolution can provide abundant information for footwear design, sports performance analysis, as well as gait and posture research.

In addition, the capability of the smart insole in monitoring foot pressure and temperature under different temperature settings was evaluated. As shown in FIG. 20A and FIG. 6H, when a cold foot (the foot was immersed into cold water of 15° C. for a while and quickly dried with a towel) is first stepped on the insole for a while and then taken off, the recorded foot temperature shows rapid drop from 24.5° C. to ≈19.5° C. and then recovers slowly. In contrast, when a hot foot (the foot was immersed into hot water of 45° C. for a while and quickly dried with a towel) steps on the insole for a while (FIG. 20B and FIG. 6I), the measured average foot temperature exhibits a rise from 24.5° C. to ≈32.8° C., which is higher than normal foot skin temperature. These results verify that the smart insole is capable of monitoring foot temperature continuously. Notably, the foot pressure distributions detected under different foot temperature (FIG. 6E for normal foot, FIG. 6H for a cold foot, and FIG. 6I for a hot foot) are similar to each other, demonstrating that temperature change does not impact the pressure mapping capability of the smart insole. All the performance presented above, together with its light weight, good scalability and cost-efficiency, makes the smart insole appealing for manufacturing wearable healthcare devices, medical diagnostic systems, and smart sports products.

The present embodiments provide large-area compliant and cost-effective strategies to fabricate wearable pressure sensors via the combination of mesh-molded microstructures and printed side-by-side electrodes. The mesh-molding embodiments for pressure-sensing microstructure fabrication enable achievement of a good balance among fabrication cost, scalability, and microstructure quality (uniformity, periodicity, and tunability). The printed electrodes with side-by-side configuration endow the present pressure sensors with high sensitivity and broad working range. When compared with the reported flexible pressure sensors, the present devices show comparable performance such as low operating voltage (1 V), high sensitivity (23.87 kPa$^{-1}$), low detection limit (7.4 Pa), fast response/recovery time (25/20 ms), excellent reliability (10,000 cycles), but much better performance in terms of working range (up to 1000 kPa), sensor tunability, and capability to form self-defined sensor arrays. More importantly, the present sensors exhibit superior scalability and cost-efficiency.

Example Materials and Methods

Scalable fabrication of PDMS/CNT conductive microstructure via mesh-molding:

Stainless-steel screen meshes with different mesh counts (provided by TWP Inc.) were used to fabricate uniform, periodic and size-tunable conductive microstructures. First, a pre-cleaned screen mesh was cut into the desired size and heated on a hotplate with the temperature set to 190° C. Then, a piece of polystyrene (PS) sheet (1 mm in thickness) was placed on the heated screen mesh for 5 min to soften the PS sheet, followed by pressing the softened PS sheet with 300 kPa to transfer the mesh structure to the PS sheet. After cooling down, the screen mesh was peeled off from the PS sheet, and PS sheet with inverse mesh structure was obtained. Then, the microstructured PS sheet was used as a template, onto which a layer of multi-walled CNT (US Research Nanomaterials, Inc. >95%, OD: 10-20 nm) was spray-coated using CNT suspension (1 mg/mL, dispersed in ethyl alcohol) with an airbrush under 2.5 bars air pressure. Subsequently, PDMS precursor mixture (Dow Corning Sylgard 184; the weight ratio of base to cross-linker varies from 5:1 to 10:1) was stirred, degassed and then cast onto the PS mold with conductive CNT layer. Finally, the PDMS was cured 60 ° C. for 2 h and carefully peeled off from the micro-patterned PS mold, resulting in a uniform and periodic conductive PDMS/CNT microstructure with robust CNT layer embedded in the microstructure surface. For pressure sensor array (FIG. 5E) fabrication, a laser-cut Kapton tape mask (60 μm in thickness) was attached on the micro-patterned PS mold before spray-coating CNT, thus to create conductive CNT patterns in the eventual PDMS/CNT conductive film.

Electrode Pattern Printing:

125 μm thick polyethylene naphthalate (PEN) film with a planarized surface (Q65HA, Teijin-DuPont) was used as the substrate for inkjet printing the electrode patterns. Silver ink (Silverjet DGP 4OLT-15C, Advanced Nano Products Co., Ltd.) was printed using a Dimatix inkjet printer (DMP-2800) with 25 μm drop spacing. Subsequently, the printed electrodes were sintered (150° C. for 30 min) to create conductive patterns. For pressure sensors array preparation, a patterned electrode array with 4×4 pixels was screen-printed on PET substrate (125 μm) using silver ink (126-33, Creative Materials, Inc.). The printed electrodes were annealed at 100° C. for 10 min.

Pressure Sensor Assembly:

Pressure sensors were constructed by assembling the scalable conductive PDMS/CNT microstructure and the printed electrodes with side-by-side configuration. Specifically, microstructured PDMS/CNT conductive film was cut into small pieces with the desired size, and then fixed on top of the side-by-side electrodes using Kapton tape. The initial resistance of the sensors could be easily tuned from several kilo-ohms to hundreds of mega-ohms by adjusting the degree of tightness between the top conductive PDMS/CNT microstructure and the bottom electrodes.

Smart Insole Construction:

To fabricate an example smart insole for both foot pressure and temperature monitoring, 12 pressure sensors and 4 thermistors were employed. The electrode patterns were inkjet-printed using the conditions mentioned above. The small gap of the side-by-side electrodes was set to 200 μm for pressure sensors and 140 μm for thermistors. Then, 4 thermistors were stencil printed on top of the corresponding electrodes using a 60 μm thick laser-cut Kapton tape mask and a glass slide. The thermistors were comprised of 6:2:1 weight ratio of NiO nanopowder (<50 nm, Sigma-Aldrich), SSBR binder (Targray Technology), and deionized (DI) water. The printed thermistors were then sintered for 2 h at 140 ° C. After that, 12 pressure sensors were constructed by placing 12 pieces of microstructured PDMS/CNT conductive films (4 mm×6 mm, with 5:1 base to cross-linker ratio) of the residual pixels of the printed electrodes. Finally, the thermistors and pressure sensors were encapsulated by attaching a layer of 60 μm thick Kapton tape on the top of the whole insole to avoid electrode scratching and the effect of moisture on the thermistors.

Characterization and Measurement:

Electrical resistance measurements were performed using a Keithley 2400 Source Meter. The electrical signal of the sensors was collected on a Keithley 2601A Source Meter and Agilent Semiconductor Device Analyzer (B1500A). The optical observation was conducted on an optical microscope (Eclipse 50i, Nikon). A Dektak profiler (Veeco 6M) was used for profile measurement. SEM observation was carried out on a Zeiss microscope with EHT value of 5 kV. Pressure measurement was conducted on a custom setup based on a computer-controlled movable stage and a force gauge (M5, Mark-10). Human physiological activities monitoring experiments performed on human subjects were carried out with informed consent under the approval of the University of California, Berkeley Institutional Review Board, protocol ID number 2018-11-11567.

Comparison in Pressure Sensing Behaviors of Three Different Electrode Configurations The pressure sensing behaviors of: 1) side-by-side electrodes (FIG. 3E), 2) microstructure vs counter electrode (FIG. 3F), and 3) interlocked conductive microstructures (FIG. 3G) were compared. For interlocked conductive microstructures, the sensitivity is very high in the beginning (0-50 kPa) as indicate in FIGS. 3H-3I. However, the signal variation becomes very sluggish subsequently, which means very narrow working range (limited to 50 kPa). This is because both layers of the interlocked conductive microstructures are soft and elastic, and they could come into full contact with each other under small pressure. Hence, pressure sensors based on this configuration are suitable to detect small pressure but not capable to detect relatively large pressure.

For side-by-side electrode and microstructure vs counter electrode configurations, the former shows larger resistance variation (see FIG. 3H) and much higher sensitivity (see FIG. 3I). From the schematic illustrations and resistance models (FIGS. 3E-3F), one can see that there are two contact resistors ($R_{contact}$) and one gap resistor ($R_{gap}$) in side-by-side electrode circuit. In microstructure vs counter electrode circuit, there are only one $R_{contact}$ and one intrinsic resistor ($R_{intrinsic}$) which arises from the conductive microstructure of certain length. In the beginning, $R_{contact}$ is much higher than $R_{gap}$ and $R_{intrinsic}$, and plays a dominative role in the whole electrical circuit. Thus, the initial resistance of side-by-side electrodes is higher than that of top-bottom microstructure vs counter electrode, as can be seen in FIG. 3H. However, with pressure applied on the sensor, $R_{contact}$ decreases dramatically and becomes smaller than $R_{gap}$ and $R_{intrinsic}$. So, $R_{gap}$ and $R_{intrinsic}$ become the dominating parts in the electrical circuit. Due the fact that $R_{gap}$ is much smaller than $R_{intrinsic}$, the final resistance of side-by-side electrodes is much lower than that of microstructure vs counter electrode (FIG. 3H). Therefore, the side-by-side electrodes show higher resistance initially but lower resistance finally when compared to microstructure vs counter electrode. As a result, the resistance variation of the side-by-side electrodes is more dramatic, thus resulting in higher sensitivity.

REFERENCES

1. X. Wang, Y. Gu, Z. Xiong, Z. Cui, and T. Zhang. Silk-molded flexible, ultrasensitive, and highly stable electronic skin for monitoring human physiological signals. *Adv. Mater.* 26, 1336-1342 (2014).
2. M. Jian, K. Xia, Q. Wang, Z. Yin, H. Wang, C. Wang, H. Xie, M. Zhang, and Y. Zhang. Flexible and highly sensitive pressure sensors based on bionic hierarchical structures. *Adv. Funct. Mater.* 27, 1606066 (2017).
3. Y. Lee, J. Park, S. Cho, Y.-E. Shin, H. Lee, J. Kim, J. Myoung, S. Cho, S. Kang, C. Baig, and H. Ko. Flexible ferroelectric sensors with ultrahigh pressure sensitivity and linear response over exceptionally broad pressure range. *ACS Nano* 12, 4045-4054 (2018).
4. C.-L. Choong, M.-B. Shim, B.-S. Lee, S. Jeon, D.-S. Ko, T.-H. Kang, J. Bae, S. H. Lee, K.-E. Byun, J. Im, Y. J. Jeong, C. E. Park, J.-J. Park, and U-I. Chung. Highly stretchable resistive pressure sensors using a conductive elastomeric composite on a micropyramid array. *Adv. Mater.* 26, 3451-3458 (2014).
5. B. C.-K. Tee, A. Chortos, R. R. Dunn, G. Schwartz, E. Eason, and Z. Bao. Tunable flexible pressure sensors using microstructured elastomer geometries for intuitive electronics. *Adv. Funct. Mater.* 24, 5427-5434 (2014).
6. C. M. Boutry, Y. Kaizawa, B. C. Schroeder, A. Chortos, A. Legrand, Z. Wang, J. Chang, P. Fox, and Z. Bao. A stretchable and biodegradable strain and pressure sensor for orthopaedic application. *Nat. Electron.* 1, 314-321 (2018).
7. Z. Wang, S. Guo, H. Li, B. Wang, Y. Sun, Z. Xu, X. Chen, K. Wu, X. Zhang, F. Xing, L. Li, and W. Hu. The semiconductor/conductor interface piezoresistive effect in an organic transistor for highly sensitive pressure sensors. *Adv. Mater.* 1805630 (2018).

8. J. Park, M. Kim, Y. Lee, H. S. Lee, and H. Ko. Fingertip skin-inspired microstructured ferroelectric skins discriminate static/dynamic pressure and temperature stimuli. *Sci. Adv.* 1, e1500661 (2015).

9. J. Park, Y. Lee, J. Hong, Y. Lee, M. Ha, Y. Jung, H. Lim, S. Y. Kim, and H. Ko. Tactile-direction-sensitive and stretchable electronic skins based on human-skin-inspired interlocked microstructures. *ACS Nano* 8, 12020-12029 (2014).

10. L. Pan, A. Chortos, G. Yu, Y. Wang, S. Isaacson, R. Allen, Y. Shi, R. Dauskardt, and Z. Bao. An ultrasensitive resistive pressure sensor based on hollow-sphere microstructure induced elasticity in conducting polymer film. *Nat. Commun.* 5, 3002 (2014).

11. Y. S. Zhou, G. Zhu, S. Niu, Y. Liu, P. Bai, Q. Jing, and Z. L. Wang. Nanometer resolution self-powered static and dynamic motion sensor based on micro-grated triboelectrification. *Adv. Mater.* 26, 1719-1724 (2014).

12. C. Pang, G.-Y. Lee, T. Kim, S. M. Kim, H. N. Kim, S.-H. Ahn, and K.-Y. Suh. A flexible and highly sensitive strain-gauge sensor using reversible interlocking of nanofibres. *Nat. Mater.* 11, 795 (2012).

13. F.-R. Fan, L. Lin, G. Zhu, W. Wu, R. Zhang, and Z. L. Wang. Transparent triboelectric nanogenerators and self-powered pressure sensors based on micropatterned plastic films. *Nano Lett.* 12, 3109-3114 (2012).

14. J.-G. Sun, T. N. Yang, I-S. Kuo, J.-M. Wu, C.-Y. Wang, and L.-J. Chen. A leaf-molded transparent triboelectric nanogenerator for smart multifunctional applications. *Nano Energy* 32, 180-186 (2017).

15. Z. Qiu, Y. Wan, W. Zhou, J. Yang, J. Yang, J. Huang, J. Zhang, Q. Liu, S. Huang, N. Bai, Z. Wu, W. Hong, H. Wang, and C. F. Guo. Ionic skin with biomimetic dielectric layer templated from calathea zebrine leaf. *Adv. Funct. Mater.* 28, 1802343 (2018).

16. Y. Pang, K. Zhang, Z. Yang, S. Jiang, Z. Ju, Y. Li, X. Wang, D. Wang, M. Jian, Y. Zhang, R. Liang, H. Tian, Y. Yang, and T.-L. Ren. Epidermis microstructure inspired graphene pressure sensor with random distributed spinosum for high sensitivity and large Linearity. *ACS Nano* 12, 2346-2354 (2018).

17. Q.-J. Sun, X.-H. Zhao, Y. Zhou, C.-C. Yeung, W. Wu, S. Venkatesh, Z.-X. Xu, J. J. Wylie, W.-J. Li, and V. A. L. Roy. Fingertip-skin-inspired highly sensitive and multifunctional sensor with hierarchically structured conductive graphite/polydimethylsiloxane foams. *Adv. Funct. Mater.* 1808829 (2019).

18. C. M. Boutry, M. Negre, M. Jorda, 0. Vardoulis, A. Chortos, 0. Khatib, and Z. Bao. A hierarchically patterned, bioinspired e-skin able to detect the direction of applied pressure for robotics. *Sci. Robot.* 3, eaau6914 (2018).

19. C.-B. Huang, S. Witomska, A. Aliprandi, M.-A. Stoeckel, M. Bonini, A. Ciesielski, and P. Samorì. Molecule-graphene hybrid materials with tunable mechanoresponse: Highly sensitive pressure sensors for health monitoring. *Adv. Mater.* 1804600 (2018).

20. S. Lee, A. Reuveny, J. Reeder, S. Lee, H. Jin, Q. L, T. Yokota, T. Sekitani, T. Isoyama, Y. Abe, Z. Suo, and T. Someya. A transparent bending-insensitive pressure sensor. *Nat. Nanotech.* 11, 472-479 (2016).

21. H.-B. Yao, J. Ge, C.-F. Wang, X. Wang, W. Hu, Z.-J. Zheng, Y. Ni, and S.-H. Yu. A flexible and highly pressure-sensitive graphene-polyurethane sponge based on fractured microstructure design. *Adv. Mater.* 25, 6692-6698 (2013).

22. R. Li, Y. Si, Z. Zhu, Y. Guo, Y. Zhang, N. Pan, G. Sun, and T. Pan. Supercapacitive iontronic nanofabric sensing. *Adv. Mater.* 1700253 (2017).

23. X. Wu, Y. Han, X. Zhang, Z. Zhou, and C. Lu. Large-area compliant, low-cost, and versatile pressure-sensing platform based on microcrack-designed carbon black@polyurethane sponge for human-machine interfacing. *Adv. Funct. Mater.* 26, 6246-6256 (2016).

24. H. Park, Y. R. Jeong, J. Yun, S. Y. Hong, S. Jin, S.-J. Lee, G. Zi, and J. S. Ha. Stretchable array of highly sensitive pressure sensors consisting of polyaniline nanofibers and Au-coated polydimethylsiloxane micropillars. *ACS Nano* 9, 9974-9985 (2015).

25. B. Zhu, Z. Niu, H. Wang, W. R. Leow, H. Wang, Y. Li, L. Zheng, J. Wei, F. Huo, and X. Chen. Microstructured graphene arrays for highly sensitive flexible tactile sensors. *Small* 10, 3625-3631 (2014).

26. S. Gong, W. Schwalb, Y. Wang, Y. Chen, Y. Tang, J. Si, B. Shirinzadeh, and W. Cheng. A wearable and highly sensitive pressure sensor with ultrathin gold nanowires. *Nat. Commun.* 5, 3132 (2014).

27. Y. Ma, N. Liu, L. Li, X. Hu, Z. Zou, J. Wang, S. Luo, and Y. Gao. A highly flexible and sensitive piezoresistive sensor based on MXene with greatly changed interlayer distances. *Nat. Commun.* 8, 1207 (2017).

28. N. Luo, Y. Huang, J. Liu, S.-C. Chen, C. P. Wong, and N. Zhao. Hollow-structured graphene-silicone-composite-based piezoresistive sensors: Decoupled property tuning and bending reliability. *Adv. Mater.* 29, 1702675 (2017).

29. G. Y. Bae, S. W. Pak, D. Kim, G. Lee, D. H. Kim, Y. Chung, and K. Cho. Linearly and highly pressure-sensitive electronic skin based on a bioinspired hierarchical structural array. *Adv. Mater.* 28, 5300-5306 (2016).

30 N. Luo, W. Dai, C. Li, Z. Zhou, L. Lu, C. C. Y. Poon, S.-C. Chen, Y. Zhang, and N. Zhao. Flexible piezoresistive sensor patch enabling ultralow power cuffless blood pressure measurement. *Adv. Funct. Mater.* 26, 1178-1187 (2016).

31. S.-J. Woo, J.-H. Kong, D.-G. Kim, and J.-M. Kim. A thin all-elastomeric capacitive pressure sensor array based on micro-contact printed elastic conductors. *J. Mater. Chem. C* 2, 4415-4422 (2014).

32. C. M. Boutry, A. Nguyen, Q. 0. Lawal, A. Chortos, S. Rondeau-Gagné, and Z. Bao. A sensitive and biodegradable pressure sensor array for cardiovascular monitoring. *Adv. Mater.* 27, 6954-6961 (2015).

33. G. Ge, Y. Zhang, J. Shao, W. Wang, W. Si, W. Huang, and X. Dong. Stretchable, transparent, and self-patterned hydrogel-based pressure sensor for human motions detection. *Adv. Funct. Mater.* 1802576 (2018).

34. C. Deng, W. Tang, L. Liu, B. Chen, M. Li, and Z. L. Wang. Self-powered insole plantar pressure mapping system. *Adv. Funct. Mater.* 1801606 (2018).

35. S. Chen, B. Zhuo, and X. Guo. Large area one-step facile processing of microstructured elastomeric dielectric film for high sensitivity and durable sensing over wide pressure range. *ACS Appl. Mater. Interfaces* 8, 20364-20370 (2016).

36. S. A . Bus. Innovations in plantar pressure and foot temperature measurements in diabetes. *Diabetes Metab. Res. Rev.* 32, 221-226 (2016).

37. J. T.-M. Cheung, and M. Zhang. A 3-dimensional finite element model of the human foot and ankle for insole design. *Arch. Phys. Med. Rehabil.* 86, 353-358 (2005).

38. N. Papanas, K. Papatheodorou, D. Papazoglou, S. Kotsiou, and E. Maltezos. Association between foot temperature and sudomotor dysfunction in type 2 diabetes. *J. Diabetes Sci. Technol.* 4, 803-807 (2010).

39. C.-C. Huang, Z.-K. Kao, and Y.-C. Liao. Flexible miniaturized nickel oxide thermistor arrays via inkjet printing technology. ACS Appl. Mater. Interfaces 5, 12954-12959 (2013).

40. Y. Khan, M. Garg, Q. Gui, M. Schadt, A. Gaikwad, D. Han, N. A. D. Yamamoto, P.Hart, R. Welte, W. Wilson, S. Czarnecki, M. Poliks, Z. Jin, K. Ghose, F. Egitto, J. Turner, A. C. Arias. Flexible hybrid electronics: Direct interfacing of soft and hard electronics for wearable health monitoring. Adv. Funct. Mater. 26, 8764-8775 (2016).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the disclosed subject matter (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or example language (e.g., "such as") provided herein, is intended merely to better illuminate the disclosed subject matter and does not pose a limitation on the scope of the invention unless otherwise claimed. No language in the specification should be construed as indicating any non-claimed element as essential to the practice of the invention.

Certain embodiments are described herein. Variations of those embodiments may become apparent to those of ordinary skill in the art upon reading the foregoing description. The inventors expect skilled artisans to employ such variations as appropriate, and the inventors intend for the embodiments to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A method of making a flexible pressure sensor, the method comprising:
   forming a first layer including a plurality of pressure-sensitive microstructures, wherein the forming the first layer includes:
      forming a polymer template having an inverse mesh structure by hot-pressing a screen mesh into a surface of a polymer substrate;
      removing the screen mesh from the polymer substrate to form the polymer template having an inverse mesh microstructure;
      forming a conductive microstructured film on the polymer template; and
      removing the conductive microstructured film from the polymer template, the conductive microstructured film including a conductive material embedded in a silicone material; and
   forming a second layer including one or more electrode pairs, each of the one or more electrode pairs comprising a first electrode positioned adjacent a second electrode on the second layer; and
   attaching the first layer to the second layer, wherein the first layer includes no electrodes formed thereon in proximity to the one or more electrode pairs of the second layer.

2. The method of claim 1, wherein the forming the conductive microstructured film on the polymer template includes applying the conductive material on the polymer template having the inverse mesh microstructure, casting an elastomer precursor material on the polymer template, and curing or drying the elastomer precursor to form the conductive microstructured film.

3. The method of claim 1, wherein the conductive material comprises a conductive carbon nanotube (CNT) material, and the silicone material comprises polydimethylsiloxane (PDMS).

4. The method of claim 1, wherein the polymer template comprises polystyrene (PS).

5. The method of claim 1, wherein the forming the second layer comprises
   printing a conductive ink pattern on a flexible polymer substrate to form the one or more electrode pairs on the flexible polymer substrate.

6. The method of claim 5, wherein the flexible polymer substrate comprises polyethylene naphthalate (PEN).

7. The method of claim 5, wherein the conductive ink comprises a silver ink.

8. The method of claim 5, wherein the printing comprises inkjet printing.

* * * * *